(12) United States Patent
El-Nokaly et al.

(10) Patent No.: US 7,416,735 B2
(45) Date of Patent: Aug. 26, 2008

(54) EMULSION COMPOSITIONS

(75) Inventors: Magda El-Nokaly, Cincinnati, OH (US); Michael Lee Vatter, Okeana, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 739 days.

(21) Appl. No.: 10/402,556

(22) Filed: Mar. 28, 2003

(65) Prior Publication Data

US 2003/0228339 A1 Dec. 11, 2003

Related U.S. Application Data

(60) Provisional application No. 60/368,491, filed on Mar. 28, 2002.

(51) Int. Cl.
- A61K 9/00 (2006.01)
- A61K 9/14 (2006.01)
- A61K 33/00 (2006.01)

(52) U.S. Cl. .................. 424/400; 424/489; 424/600; 514/937

(58) Field of Classification Search ................ 424/401, 424/489; 514/937, 938; 454/400, 489, 600
See application file for complete search history.

(56) References Cited

U.S. PATENT DOCUMENTS

| | | | |
|---|---|---|---|
| 3,380,853 A | 4/1968 | Angelis | |
| 4,665,107 A | 5/1987 | Micale | |
| 4,742,963 A | 5/1988 | Mervaldi | |
| 5,143,722 A | 9/1992 | Hollenberg et al. | |
| 5,223,559 A | 6/1993 | Arraudeau et al. | |
| 5,326,392 A | 7/1994 | Miller et al. | |
| 5,476,660 A | 12/1995 | Somasundaran et al. | |
| 5,545,428 A | 8/1996 | Crimp et al. | |
| 5,716,671 A | 2/1998 | Pak et al. | |
| 5,776,241 A | 7/1998 | Giacomoni et al. | |
| 6,007,826 A | 12/1999 | Benita et al. | |
| 6,083,491 A | 7/2000 | Mellul et al. | |
| 6,432,417 B1 | 8/2002 | Mellul et al. | |
| 2002/0054890 A1 * | 5/2002 | Gers-Barlag et al. | 424/401 |

FOREIGN PATENT DOCUMENTS

| | | |
|---|---|---|
| EP | 0 577 817 B1 | 1/1994 |
| EP | 680 745 A2 | 11/1995 |
| EP | 689 827 A1 | 1/1996 |
| EP | 728 473 A1 | 8/1996 |
| EP | 727662 A1 | 8/1996 |
| EP | 0 504 066 B1 | 9/1996 |
| EP | 0 529 883 B1 | 1/1997 |
| EP | 0 992 233 A2 | 4/2000 |
| FR | 2723311 A1 | 2/1996 |
| FR | 2730811 A1 | 8/1996 |
| FR | 2773990 | 7/1999 |
| JP | 2581920 | 5/1987 |
| WO | WO-93/18852 | 9/1993 |
| WO | WO 95/09599 A1 | 4/1995 |
| WO | WO 95/22311 | 8/1995 |
| WO | WO 99/24001 A1 | 5/1999 |
| WO | WO 99/47253 | 9/1999 |
| WO | WO 99/54053 A1 | 10/1999 |
| WO | WO 00/74519 A2 | 12/2000 |
| WO | WO 02/03931 A2 | 1/2002 |
| WO | WO 02/062310 A1 | 8/2002 |

OTHER PUBLICATIONS

Lee, J., et al., "Preparation of Ultrafine Fe304 Particles by Precipitation in the Presence of PVA at High pH"; *Journal of Colloid and Interface Science*; 1996, V. 177, Art. 0062, pp. 490-494, Academic Press, Inc.

Driscoll, P., "Treated Pigments in Decorative Cosmetics"; *Cosmetics & Toiletries*; Jul. 1989 vol. 104 pp. 43-45; United States.

Tohver, V., et al., "Nanoparticle halos: A new colloid stabilization mechanism"; PNAS Early Edition; United States.

(Continued)

*Primary Examiner*—Johann R. Richter
*Assistant Examiner*—Konata M. George
(74) *Attorney, Agent, or Firm*—Andrew J. Hagerty; Steven Robert Chuey; Jay A. Krebs

(57) ABSTRACT

The present invention relates to particle stabilizing compositions suitable for use in fabric care products, home care products, diapers, incontinence articles, feminine care products, pharmaceuticals, oral care products, antiperspirants, deodorants, personal cleansing products, skin care products and hair care products comprising: a) an emulsion comprising from about 1% to about 99% by weight of the emulsion of an internal phase and from about 1% to about 99% by weight of the emulsion of an external phase; b) a charged species that is present in the emulsion; and c) charged insoluble solid particles which are dispersed in the emulsion wherein the charged species possesses a charge which is opposed to that of the charged insoluble solid particles and wherein essentially all of the charged species and charged insoluble solid particles accumulate at the interface of the emulsion and wherein Brownian motion is not exhibited by the charged insoluble solid particles.

4 Claims, No Drawings

OTHER PUBLICATIONS

Brown, D., "Suspended in space: Researchers make important discovery about materials"; NASA.gov/releases/01-154.html; Jul. 31, 2001; Washington, DC.

Matijevie, E., "Monodispersed Colloids: Preparations and interactions"; *Progr Colloid Polym Science* 1996 vol. 101 pp. 38-44 Copywrite Steinkopff Verlag 1996 New York.

Sunkel, J.M., et al., "The Stability Behavior of Sol-Emulsion Systems"; *Journal of Colloid and Interface Science*; vol. 179, 1996 p. 618.

Tambe, L.E., et al., "Factors Controlling the Stability of Colloid-Stabilized Emulsions"; *Journal of Colloid and Interface Science*; vol. 157 1993 pp. 244-253.

Tachowicz, T., et al., "Heterocoagulation of Silicone Emulsions on Keratin Fibers"; *Journal of Colloid & Interface Science*; vol. 133 No. 1 1989.

Usui, S., "Heterorcoagulation".

*Surfactant Systems, Their Chemistry, Pharmacy and Biology*, Attwood & Florence, Ed., Chapman & Hall Publishers (1983), ISBN 0-412-14840-4—Book not included.

*Food Emulsions*, Friberg, S., Ed, Marcell Dekker, Inc., Publishers, New York and Basel, (1976) ISBN 0-8247-6337-8—Book not included.

*Foundations of Colloid Science*, vol. 1, Hunter, R. J., Ed.; Oxford University Press, Publishers, New York, (1987) ISBN 0-19-855188-6—Book not included.

* cited by examiner

EMULSION COMPOSITIONS

CROSS REFERENCE TO RELATED APPLICATION

This application claims the benefit of U.S. Provisional Application No. 60/368,491, filed Mar. 28, 2002.

TECHNICAL FIELD

The present invention relates to emulsion compositions which can uniformly deposit insoluble solid particles upon a substrate. Particularly, the present invention relates to pigmented emulsion cosmetic compositions which provide a natural appearance to the skin upon application. More particularly, these cosmetic compositions are formulated such that agglomeration of the pigment in the product and upon application to the skin is minimized.

BACKGROUND OF THE INVENTION

Foundation products are typically applied to the entire face to mask perceived imperfections in skin texture (e.g., fine lines and wrinkles), pigmentation or vascularization. It is desirable for foundations to mask these imperfections and yet still allow for a natural appearance of the skin. In other words, consumers want good coverage from a foundation product, but do not want the appearance of too much make-up, e.g., a cakey appearance.

Pigmented oil-in-water and water-in-oil emulsion foundations are a popular type of foundation product available on the market today. These products are relatively inexpensive and are easy to apply to the skin. Moreover, the pigmented oil-in-water or water-in-oil emulsion foundations lend themselves to variation in pigment type and level to give different degrees of color coverage and albedo of the face.

It is believed, however, that, in order to minimize the appearance of fine lines and wrinkles and to avoid a cakey appearance when utilizing a foundation product, it is important to deposit the pigment from the foundation product uniformly on the skin. Unfortunately, the tendency of the pigment is to agglomerate (i.e., flocculate) in the foundation product and, upon application of the foundation product to the skin, to either collect in the fine lines and wrinkles or agglomerate on the skin, thereby accentuating, rather than minimizing, the appearance of the fine lines or wrinkles, and further delivering a cakey, unnatural appearance to the skin.

Preventing agglomeration or flocculation of the pigment both in a foundation product and upon its application to the skin can be very difficult. One way to improve the stability of the pigments in foundation products is to "coat" the pigment, e.g., by adsorbing certain materials onto the surface of the pigment, wet ball milling or plasma treatment. See, e.g., Driscoll, P., "Treated Pigments in Decorative Cosmetics", *Cosmetics and Toiletries*, Vol. 104 (July 1989), pp 43-45. For example, foundation and other personal care products containing hydrophobically- or hydrophilically-coated pigments are known in the art. (See, for example, Lee, J. et al., "Preparation of Ultra Fine $Fe_3O_4$ Particles by Precipitation in the Presence of PVA at High pH", *J. Colloid Interface Sci.*, 177, p. 490 (1996) and European Patent Application 504,066, published Mar. 13, 1992). There is, however, an ongoing need for cosmetic foundations that exhibit lesser agglomeration of pigments in the product itself and when applied to skin. More importantly, there is a need to provide products that meet consumer needs with respect to the natural appearance of the skin when the product is applied.

It has now surprisingly been found that foundation products, wherein agglomeration of the pigment contained therein is minimized, can be formulated using the technology hereinafter described. Moreover, when the foundation products of the present invention are applied to the skin, the pigment remains essentially unagglomerated and is therefore capable of being uniformly deposited on the skin. Accordingly, good coverage of the skin and a natural appearance of the skin is provided. This is a surprising development, given that the use of oppositely charged particles in cosmetic formulations is typically avoided due to interactions which create negative effects.

It has also now been surprisingly found that products useful in fabric care products, home care products, diapers, incontinence articles, feminine care products, pharmaceuticals, oral care products, antiperspirants, deodorants, personal cleansing products, skin care products and hair care products, wherein agglomeration of the composition contained therein is minimized, can be formulated using the technology hereinafter described. Moreover, since the claimed composition remains essentially unagglomerated, it can also be utilized in the above disclosed consumer fields deposited on a substrate. Accordingly, good coverage of the substrate with the uniformly dispersed composition allows for enhanced improvements in the care of fabrics, skin, hair, and teeth.

SUMMARY OF THE INVENTION

The present invention relates to a particle stabilizing composition comprising:
a) an emulsion, comprising from about 1% to about 99%, by weight of the emulsion, of an internal phase and from about 1% to about 99%, by weight of the emulsion, of an external phase;
b) a charged species that is present in the emulsion; and
c) charged insoluble solid particles which are dispersed in said emulsion;
wherein the charged species possesses a charge which is opposed to that of the charged insoluble solid particles and wherein essentially all of the charged species and charged insoluble solid particles accumulate at the interface of the emulsion and wherein Brownian motion is not exhibited by the charged insoluble solid particles.

In addition to the charged species and particles within the present invention, the composition may also comprise additional charged or even uncharged particulate material dispersed in the emulsion.

DETAILED DESCRIPTION OF THE INVENTION

The present invention relates to compositions, particularly cosmetic compositions which provide a natural appearance to the substrate to which it is applied (e.g., hair, skin, and/or nails), and especially foundation compositions. In particular, the cosmetic compositions of the present invention are formulated such that agglomeration of an insoluble solid particle in the product and on the skin is minimized. In cosmetic compositions, the insoluble solid particle of the present invention may be a pigment. Using the present invention in foundations, the pigment has a significantly reduced tendency to collect in the fine lines or wrinkles (or otherwise agglomerate on the skin), a cakey appearance is avoided and the skin has a natural appearance. Without being bound or limited by theory, it is believed that as a result of minimizing agglomeration of the pigment, the pigment is uniformly distributed throughout the product and that, upon application to the skin, the pigment in the composition is uniformly deposited on the skin as perceived by the eye. In any event, the distribution of the pigment and/or its appearance on the skin becomes substantially independent of skin topography.

As used herein, the term "cosmetic compositions" refers to compositions for application to the hair, nails and/or skin, especially the face, which contain at least about 0.01% and up to about 50% of pigment as hereinafter defined. Cosmetic compositions include, but are not limited to, foundations, blush, mascara, eyeshadow, eyeliner, lipstick, nail polish and tinted moisturizers. The invention described herein is particularly suited for foundation compositions. As used herein, the term "foundation" refers to a liquid, solid or semi-solid facial skin cosmetic composition which includes, but is not limited to, lotions, creams, gels, serums, compacts, sticks and pastes all of which may or may not be applied using an applicator, substrate, sponge, a combination thereof or a similar means or some type of mechanical delivery such as air brush, electrostatic spray, a combination thereof or a similar means.

The benefits of the present invention are most apparent for liquid foundations and solid compact emulsion foundations. As used herein, "liquid foundations" refers to liquid or cream type foundation products which may range from thin liquids which are pourable (i.e., from a bottle) to viscous gels or creams which are often packaged in jars, tubes or pump-type dispensers. Liquid foundations typically have viscosities in the ranges of from about 10 to about 10,000 centipoise measured at a shear rate of 100 1/s. Viscosity can be measured using a typical rotational viscometer such as a Haake RS100 with 35/1 degree cone and plate geometry or the equivalent thereof. The viscosity is determined on the composition after the composition has been allowed to stabilize following its preparation, generally at least 24 hours under the conditions of 25° C.±1° C. and an ambient pressure and is measured with the composition at a temperature of 25° C.±1° C., after 30 seconds rotation. Liquid foundations are typically applied to the skin by finger.

As used herein, "solid compact emulsion foundations" means foundations compositions which are made from an emulsion which is gelled to a solid or semi-solid state, for example, by a solid wax-like network, liquid crystals, polymers, surfactant/polymer/protein mixtures, etc. Due to their solid or semi-solid consistency, solid emulsions are typically characterized by their hardness, which can be measured by their resistance to penetration by a probe or needle which is dropped or pushed into the solidfied composition. Hardness can be measured using typically penetrometers such as a Voland-Stevens LFRA Texture Analyzer available from Texture Technologies Corp. with Stevens probe #TA-PG (5 mm diameter Cylinder) or equivalent thereof. Solid emulsion foundations typically have a hardness in the range of 30-500 grams force as measured as the minimum force required to push a cylinder of 5 mm diameter to a depth of 3 mm into the composition at a speed of 0.2 mm/second. Hardness is determined after the composition has been allowed to stabilize following its preparation, generally at least 24 hours under the conditions of 25° C.±1° C. and ambient pressure and is measured with the composition at a temperature of 25° C.±1° C. Solid emulsion foundations include for example compacts and sticks, and are typically packaged in a compact or plastic cylinder and are typically applied to the skin by finger or sponge applicator. Typically, the foundations are used over a large area of skin, such as the face and neck.

As used herein, an "emulsion composition" means a composition comprising at least two distinct phases known as the internal phase and the external phase.

As used herein, the term "internal phase" of the emulsion composition is the phase wherein the material or materials of said phase are dispersed as small particles within another distinct phase of the emulsion composition.

As used herein, the term "external phase" of the emulsion composition is the phase wherein the internal phase is dispersed within.

Preferred compositions of the present invention are formulated such that the aqueous phase of the composition (whether as the internal phase or as the external phase) has a pH ranging from about 5 to about 10, more preferably from about 6 to about 8, most preferably from about 6.5 to about 7.5, although the benefits of the invention (natural appearance cosmetics) can be achieved at pHs as low as 2. The cosmetic compositions herein can be applied by any conventional means including, for example, with the fingers, with an applicator such as a brush or a sponge, or via aerolization, including, for example, airbrush or electrostatic spray devices.

The compositions of the present invention, including the materials contained therein and processes for making them, are described in detail as follows.

I. Materials

The compositions of the present invention are comprise the following materials:

A. The Emulsion

The compositions of the present invention comprise an emulsion, wherein the internal phase can be a liquid, gas, solid, liquid crystal, gel, or combinations thereof. In preferred embodiments, the emulsion is selected from the group consisting of water-in-oil emulsions, oil-in-water emulsions, water-in-silicone, silicone-in-water, water-in-silicone elastomer emulsions, silicone elastomer-in-water emulsions and combinations thereof. Preferably an oil-in-water or water-in-oil emulsion is used. More preferably, compositions of the present invention comprise water-in-oil emulsions. When the compositions of the present invention are used as cosmetic products, the compositions typically comprise from about 50% to about 99.9%, preferably from about 70% to about 95%, more preferably from about 80% to about 90%, of an emulsion. Solid emulsion compact foundation compositions of the present invention typically comprise from about 50% to about 99.9%, preferably from about 60% to about 99.9%, more preferably from about 70% to about 99.9%, by weight of the composition, of an emulsion. Liquid foundation compositions typically comprise from about 80% to about 99.9%, by weight of the composition, of an emulsion.

The emulsion may also contain an anti-foaming agent to minimize foaming upon application to a substrate. Anti-foaming agents include high molecular weight silicones and other materials well known in the art for such use.

Suitable emulsions may have a wide range of viscosities, depending on the desired product form. Exemplary low viscosity emulsions, which are preferred, have a viscosity of about 50 centistokes or less, more preferably about 10 centistokes or less, and most perferably from about 5 centistokes or less.

The emulsion comprises an internal (i.e., dispersed) phase and an external phase. When water is the internal phase (i.e., the aqueous phase of water-in-oil or water-in-silicone emulsion), the emulsion typically comprises from about 1% to about 99%, preferably from about 15% to about 90%, more preferably from about 40% to about 85%, by weight of the emulsion. When water is the external phase, the emulsion typically comprises from about 1% to about 99%, preferably from about 10% to about 85%, more preferably from about 15% to about 60%, by weight of the emulsion. Highly concentrated emulsions wherein the internal phase comprises a high proportion of the emulsion and wherein the proportion of the external phase is minimized, are very stable and are, therefore, preferred herein.

The internal phase is typically in the form of droplets which typically range in size from about 0.15 to about 40 microns in diameter, preferably from about 0.20 to about 30 microns and most preferably from about 0.25 to about 20 microns. The particle size of the droplets comprising the internal phase of the emulsion can be determined as described in the "Analytical Methods" section hereinafter.

It is understood that the oil phase of the emulsions herein (whether as the external phase or as the internal phase) can comprise a wide variety of hydrophobic and other components. Numerous examples can be found in Sagarin, *Cosmetics, Science and Technology*, 2nd edition, Vol. 1, pp. 32-43 (1972), and Cosmetic Bench Reference, Cosmetics & Toiletries, pp. 1.19-1.22 (1996) herein incorporated by reference. Nonlimiting examples of suitable hydrophobic components for use in the compositions herein include those selected from the group consisting of:

(i) Mineral oil, which is also known as petrolatum liquid, is a mixture of liquid hydrocarbons obtained from petroleum. See, The Merck Index, Tenth Edition, Entry 7048, p. 1033 (1983) and International Cosmetic Ingredient Dictionary, Fifth Edition, vol. 1, p. 415-417 (1993), which are incorporated by reference herein in their entirety.

(ii) Petrolatum, which is also known as petroleum jelly, is a colloidal system of nonstraight-chain solid hydrocarbons and high-boiling liquid hydrocarbons, in which most of the liquid hydrocarbons are held inside the micelles or micelle-like self assembled aggregates. See, The Merck Index, Tenth Edition, Entry 7047, p. 1033 (1983); Schindler, *Drug. Cosmet. Ind.*, 89, 36-37, 76, 78-80, 82 (1961); and International *Cosmetic* Ingredient Dictionary, Fifth Edition, vol. 1, p. 537 (1993), which are incorporated by reference herein in their entirety.

(iii) Straight and branched chain hydrocarbons having from about 7 to about 40 carbon atoms. Nonlimiting examples of these hydrocarbon materials include dodecane, isododecane, squalane, cholesterol, hydrogenated polyisobutylene, dodecosane (i.e. a $C_{22}$ hydrocarbon), hexadecane, isohexadecane (a commercially available hydrocarbon sold as Permethyl® 101A by Presperse, South Plainfield, N.J.). Also useful are the C7-C40 isoparaffins, which are C7-C40 branched hydrocarbons.

(iv) C1-C30 alcohol esters of C1-C30 carboxylic acids and of C2-C30 dicarboxylic acids, including straight and branched chain materials as well as aromatic derivatives (as used herein in reference to the hydrophobic component, mono- and poly-carboxylic acids include straight chain, branched chain and aryl carboxylic acids). Nonlimiting examples include isononyl isononanoate, methyl isostearate, ethyl isostearate, diisopropyl sebacate, diisopropyl adipate, isopropyl myristate, isopropyl palmitate, methyl palmitate, myristyl propionate, 2-ethylhexyl palmitate, isodecyl neopentanoate, di-2-ethylhexyl maleate, cetyl palmitate, myristyl myristate, stearyl stearate, isopropyl stearate, methyl stearate, cetyl stearate, behenyl behenate, dioctyl maleate, dioctyl sebacate, diisopropyl adipate, cetyl octanoate, diisopropyl dilinoleate.

(v) Mono-, di- and tri-glycerides of C1-C30 carboxylic acids, e.g., caprylic/capric triglyceride, PEG-6 caprylic/capric triglyceride, PEG-8 caprylic/capric triglyceride.

(vi) Alkylene glycol esters of C1-C30 carboxylic acids, e.g., ethylene glycol mono- and di-esters, and propylene glycol mono- and di-esters of C1-C30 carboxylic acids e.g., ethylene glycol distearate.

(vii) Propoxylated and ethoxylated derivatives of the foregoing materials.

(viii) C1-C30 mono- and poly-esters of sugars and related materials. These esters are derived from a sugar or polyol moiety and one or more carboxylic acid moieties. Depending on the constituent acid and sugar, these esters can be in either liquid or solid form at room temperature. Examples of liquid esters include: glucose tetraoleate, the glucose tetraesters of soybean oil fatty acids (unsaturated), the mannose tetraesters of mixed soybean oil fatty acids, the galactose tetraesters of oleic acid, the arabinose tetraesters of linoleic acid, xylose tetralinoleate, galactose pentaoleate, sorbitol tetraoleate, the sorbitol hexaesters of unsaturated soybean oil fatty acids, xylitol pentaoleate, sucrose tetraoleate, sucrose pentaoletate, sucrose hexaoleate, sucrose hepatoleate, sucrose octaoleate, and mixtures thereof. Examples of solid esters include: sorbitol hexaester in which the carboxylic acid ester moieties are palmitoleate and arachidate in a 1:2 molar ratio; the octaester of raffinose in which the carboxylic acid ester moieties are linoleate and behenate in a 1:3 molar ratio; the heptaester of maltose wherein the esterifying carboxylic acid moieties are sunflower seed oil fatty acids and lignocerate in a 3:4 molar ratio; the octaester of sucrose wherein the esterifying carboxylic acid moieties are oleate and behenate in a 2:6 molar ratio; and the octaester of sucrose wherein the esterifying carboxylic acid moieties are laurate, linoleate and behenate in a 1:3:4 molar ratio. A preferred solid material is sucrose polyester in which the degree of esterification is 7-8, and in which the fatty acid moieties are C18 mono- and/or di-unsaturated and behenic, in a molar ratio of unsaturates:behenic of 1:7 to 3:5. A particularly preferred solid sugar polyester is the octaester of sucrose in which there are about 7 behenic fatty acid moieties and about 1 oleic acid moiety in the molecule. Other materials include cottonseed oil or soybean oil fatty acid esters of sucrose. The ester materials are further described in, U.S. Pat. Nos. 2,831,854, 4,005,196, to Jandacek, issued Jan. 25, 1977; U.S. Pat. No. 4,005,195, to Jandacek, issued Jan. 25, 1977, U.S. Pat. No. 5,306,516, to Letton et al., issued Apr. 26, 1994; U.S. Pat. No. 5,306,515, to Letton et al., issued Apr. 26, 1994; U.S. Pat. No. 5,305,514, to Letton et al., issued Apr. 26, 1994; U.S. Pat. No. 4,797,300, to Jandacek et al., issued Jan. 10, 1989; U.S. Pat. No. 3,963,699, to Rizzi et al, issued Jun. 15, 1976; U.S. Pat. No. 4,518,772, to Volpenhein, issued May 21, 1985; and U.S. Pat. No. 4,517,360, to Volpenhein, issued May 21, 1985; all of which are incorporated by reference herein in their entirety.

(ix) Organopolysiloxane oils. The organopolysiloxane oil may be volatile, non-volatile, or a mixture of volatile and non-volatile silicones. The term "nonvolatile" as used in this context refers to those silicones that are liquid under ambient conditions and have a flash point (under one atmospheric of pressure) of or greater than about 100° C. The term "volatile" as used in this context refers to all other silicone oils. Suitable organopolysiloxanes can be selected from a wide variety of silicones spanning a broad range of volatilities and viscosities. Nonlimiting examples of suitable silicones are disclosed in U.S. Pat. No. 5,069,897, to Orr, issued Dec. 3, 1991, and Cosmetic Bench Reference, Cosmetics & Toiletries, pp. 1.33-1.34 (1996) which are incorporated by reference herein in its entirety. Examples of suitable organopolysiloxane oils include polyalkylsiloxanes, cyclic polyalkylsiloxanes, and polyalkylarylsiloxanes.

Polyalkylsiloxanes useful in the composition herein include polyalkylsiloxanes with viscosities of from about 0.5 to about 1,000,000 centistokes at 25° C. Such polyalkylsiloxanes can be represented by the general chemical formula $R_3SiO[R_2SiO]_xSiR_3$ wherein R is an alkyl group having from one to about 30 carbon atoms (preferably R is methyl or ethyl, more preferably methyl; also mixed alkyl groups can be used in the same molecule), and x is an integer from 0 to about 10,000, chosen to achieve the desired molecular weight which can range to over about 10,000,000. Commercially available polyalkylsiloxanes include the polydimethylsiloxanes, which are also known as dimethicones, examples of which include the Vicasil® series sold by General Electric Company and the Dow Corning® 200 series sold by Dow Corning Corporation. Specific examples of suitable polydimethylsiloxanes include Dow Corning® 200 fluid having a viscosity of 0.65 centistokes and a boiling point of 100° C., Dow Corning® 225 fluid having a viscosity of 10 centistokes and a boiling point greater than 200° C., and Dow Corning® 200 fluids having viscosities of 50, 350, and 12,500 centistokes, respectively, and boiling points greater than 200° C. Examples of suitable alkyl and substituted dimethicones include those represented by the chemical formula $(CH_3)_3SiO[(CH_3)_2SiO]_x[CH_3RSiO]_ySi(CH_3)_3$ wherein R is straight or branched chain alkyl having from two to about 30 carbon atoms and x and y are each integers of 1 or greater selected to achieve the desired molecular weight which can range to over about 10,000,000. Examples of these alkyl-substituted dimethicones include cetyl dimethicone and lauryl dimethicone.

Cyclic polyalkylsiloxanes suitable for use in the composition include those represented by the chemical formula $[SiR_2—O]_n$ wherein R is an alkyl group (preferably R is methyl or ethyl, more preferably methyl) and n is an integer from about 3 to about 8, more preferably n is an integer from about 3 to about 7, and most preferably n is an integer from about 4 to about 6. When R is methyl, these materials are typically referred to as cyclomethicones. Commercially available cyclomethicones include Dow Corning® 244 fluid having a viscosity of 2.5 centistokes, and a boiling point of 172° C., which primarily contains the cyclomethicone tetramer (i.e. n=4), Dow Corning® 344 fluid having a viscosity of 2.5 centistokes and a boiling point of 178° C., which primarily contains a mixture of the cyclomethicone tetramer and pentamer (i.e. n=4 and 5), Dow Corning® 245 fluid having a viscosity of 4.2 centistokes and a boiling point of 205° C., which primarily contains the cyclomethicone pentamer (i.e. n=5), and Dow Corning® 345 fluid having a viscosity of 4.5 centistokes and a boiling point of 217°, which primarily contains a mixture of the cyclomethicone tetramer, pentamer, and hexamer (i.e. n=4, 5, and 6).

Also useful are materials such as trimethylsiloxysilicate, which is a polymeric material corresponding to the general chemical formula $[(CH_2)_3SiO_{1/2}]_x[SiO_2]_y$, wherein x is an integer from about 1 to about 500 and y is an integer from about 1 to about 500. A commercially available trimethylsiloxysilicate is sold as a mixture with dimethicone as Dow Corning® 593 fluid.

Dimethiconols are also suitable for use in the composition. These compounds can be represented by the chemical formulas $R_3SiO[R_2SiO]_xSiR_2OH$ and $HOR_2SiO[R_2SiO]_xSiR_2OH$ wherein R is an alkyl group (preferably R is methyl or ethyl, more preferably methyl) and x is an integer from 0 to about 500, chosen to achieve the desired molecular weight. Commercially available dimethiconols are typically sold as mixtures with dimethicone or cyclomethicone (e.g. Dow Corning® 1401, 1402, and 1403 fluids).

Polyalkylaryl siloxanes are also suitable for use in the composition. Polymethylphenyl siloxanes having viscosities from about 15 to about 65 centistokes at 25° C. are especially useful.

Preferred for use herein are organopolysiloxanes selected from the group consisting of polyalkylsiloxanes, alkyl substituted dimethicones, cyclomethicones, trimethylsiloxysilicates, dimethiconols, polyalkylaryl siloxanes, and mixtures thereof. More preferred for use herein are polyalkylsiloxanes and cyclomethicones. Preferred among the polyalkylsiloxanes are dimethicones.

(x) Vegetable oils and hydrogenated vegetable oils. Examples of vegetable oils and hydrogenated vegetable oils include safflower oil, castor oil, coconut oil, cottonseed oil, menhaden oil, palm kernel oil, palm oil, peanut oil, soybean oil, rapeseed oil, linseed oil, rice bran oil, pine oil, sesame oil, sunflower seed oil, hydrogenated safflower oil, hydrogenated castor oil, hydrogenated coconut oil, hydrogenated cottonseed oil, hydrogenated menhaden oil, hydrogenated palm kernel oil, hydrogenated palm oil, hydrogenated peanut oil, hydrogenated soybean oil, hydrogenated rapeseed oil, hydrogenated linseed oil, hydrogenated rice bran oil, hydrogenated sesame oil, hydrogenated sunflower seed oil, and mixtures thereof.

(xi) Animal fats and oils, e.g., lanolin and derivatives thereof, cod liver oil.

(xii) Other materials: Also useful are C4-C20 alkyl ethers of polypropylene glycols, C1-C20 carboxylic acid esters of polypropylene glycols, and di-C8-C30 alkyl ethers. Nonlimiting examples of these materials include PPG-14 butyl ether, PPG-15 stearyl ether, dioctyl ether, dodecyl octyl ether, and mixtures thereof.

Preferably, the oil phase comprises silicones. More preferably from about 30% to about 95%, most preferably from about 50% to about 90% of the oil phase is volatile silicones, non-volatile silicones and mixtures thereof. Still more preferably, these silicones are chosen from cyclomethicones, trimethicones, such as methyl trimethicone, dimethicones and mixtures thereof. Thus one of the most preferred oil phases can be considered, and is thus defined as a "silicone" phase. For purposes of the present invention, the terms "water-in-oil emulsions" and "oil-in-water emulsions" encompass water-in-silicone emulsions and silicone-in-water emulsions, respectively.

B. The Charged Species

The compositions herein also comprise a charged species that possesses a charge that is opposite that of the charged insoluble solid particles (hereinafter described). This species can be present within the internal phase of the emulsion, at the interface of the emulsion, and/or in the external phase of the emulsion (in bulk). Typically and preferably, a substantial portion of the species are present at the interface of the internal phase and the external phase of the emulsion.

The species can be for example, hydrogen ion, an acid, a base, an ionic polymer, an ionic surfactant, a lipid or mixtures thereof. Ionic surfactants include cationic, anionic and amphoteric surfactants. Suitable ionic surfactants for use herein are described hereinafter in the subsection entitled "Emulsifiers".

In a highly preferred embodiment of the present invention, the species comprises an ionic polymer and is present at the interface between the internal phase and the external phase of the emulsion. In this embodiment of the invention, the emulsion droplet contains an amount of ionic polymer sufficient to cover the surface of the droplet. In particular, the present invention comprises from about 0.1% to about 25%, more preferably from about 0.5% to about 10%, and most preferably from about 0.5% to about 5%, by weight of the composition, of charged species.

Suitable anionic polymers for use in this embodiment of the invention include, but are not limited to, copolymers of polyacrylate, ammonium polyacrylate, sodium polyacrylate, potassium polyacrylate, ethylene acrylic acid copolymer, hydrolyzed wheat protein polysiloxane copolymer, dimethicone copolyol phosphate, phosphate ester, sodium chondroiton sulfate, sodium hyaluronate, ammonium hyaluronate, sodium alginate, ammonium alginate, diglycol cyclohexanedimethanol isophthalates sulfoisophthalates copolymer and mixtures therof.

Suitable cationic polymers for use in this embodiment of the invention include, but are not limited to, cellulose derivatives, polysaccharides, chitosan, derivatives of chitosan, chitosan di-pyrrolidone carboxylate, hydroxypropyl chitosan, quaterniums, quaternium-80, quaternium-61, polyquaterniums, hydroxyethyl cetyldimonium phosphate, adipic acid/dimethylaminohydroxypropyl diethyltriamine copolymer, guar hydroxypropyltrimonium chloride, dimethicone copolyol amine(s), amidomethicones, dimethicone salts and mixtures thereof.

Exemplary lipids include charged lipids which are compatible with skin such as phospholipids, simple carboxylic esters including fats (esters of fatty acids with glycerol), and waxes (sterol esters, esters of fatty acids with alcohols other than glycerol), complex carboxylic esters (glycerophospholipids, glycoglycerolipids, glycoglycerolipid sulfates), complex lipids (lipids containing amides, sphinogolipids, gylcosphingolipids), precursors and derived lipids including phosphatidic acid, bile acids, and bases such as sphinganines, hydrocarbons containing charged moieties (either straight or simple branched chain), lipid vitamins and hormones with multiple functional charged groups, and lipoproteins.

C. Charged Insoluble Solid Particles

The composition of the present invention includes charged insoluble solid particles. These charged particles of the present invention preferably have a particle size of less than 200 µm. Typically, the particles will have a particle size from about 0.001 µm to about 50 µm, still more preferably from about 0.005 µm to about 1 µm, and even more preferably from about 0.01 µm to about 0.1 µm in diameter.

Typical particle levels are selected depending upon the particular purpose of the composition. For example, where it is desired to deliver color benefits, pigment particles conferring the desired hues can be incorporated. Where the desire is to treat or prevent symptoms such as diaper rash, inflammation, and/or other skin disorders, the present invention allows for insoluble skin care agents to be delivered more uniformly to the skin. Determination of the levels and particle types is within the skill of the artisan. Particles that are generally recognized as safe, and are listed in C.T.F.A. Cosmetic Ingredient Handbook, Sixth Ed., Cosmetic and Fragrance Assn., Inc., Washington D.C. (1995), incorporated herein by reference, can be used.

In the compositions of the present invention, it is preferable to incorporate from about 0.01% to about 80%, more preferably from about 0.1% to about 50%, still more preferably from about 1% to about 30%, and most preferably from about 5% to about 20%, by weight of the composition, of charged insoluble solid particles.

The particles can be scattering or non-scattering and may or may not impart color. Suitable particles include bismuth oxychloride, titanated mica, fumed silica, spherical silica, polymethylmethacrylate, micronized teflon, boron nitride, acrylate polymers, aluminum silicate, aluminum starch octenylsuccinate, bentonite, calcium silicate, cellulose, chalk, corn starch, diatomaceous earth, fuller's earth, glyceryl starch, hectorite, hydrated silica, kaolin, magnesium aluminum silicate, magnesium carbonate, magnesium hydroxide, magnesium oxide, magnesium silicate, magnesium trisilicate, maltodextrin, montmorillonite, microcrystaline cellulose, rice starch, silica, talc, mica, titanium dioxide, zinc laurate, zinc myristate, zinc neodecanoate, zinc rosinate, zinc stearate, polyethylene, alumina, attapulgite, calcium carbonate, calcium silicate, dextran, kaolin, nylon, silica silylate, silk powder, sericite, soy flour, tin oxide, titanium hydroxide, trimagnesium phosphate, walnut shell powder, or mixtures thereof. The above mentioned particles may be surface treated with lecithin, amino acids, mineral oil, silicone oil, or various other agents either alone or in combination, which coat the powder surface and render the particles hydrophobic in nature.

Water insoluble solid particles of various shapes and densities are useful. In a preferred embodiment, the particles tend to have a spherical, an oval, an irregular, or any other shape in which the ratio of the largest dimension to the smallest dimension (defined as the aspect ratio) is less than 10. More preferably, the aspect ratio of the particles is less than 8. Still more preferably, the aspect ratio of the particles is less than 5.

Particles useful in the present invention can be nano, micro, and mixtures thereof, and can be natural, synthetic, or semisynthetic in composition. Hybrid particles are also useful. Synthetic particles can be made of either cross-linked or non cross-linked polymers. The particles of the present invention can have surface charges or their surface can be modified with organic or inorganic materials such as surfactants, polymers, and inorganic materials. Particle complexes are also useful.

Non limiting examples of natural particles include various precipitated silica particles in hydrophilic and hydrophobic forms available from Degussa-Huls under the trade name Sipernet. Snowtex colloidal silica particles available from Nissan Chemical America Corporation.

Examples of synthetic particles include nylon, silicone resins, poly(meth)acrylates, polyethylene, polyester, polypropylene, polystyrene, polyurethane, polyamide, epoxy resins, urea resins, and acrylic powders. Non limiting examples of useful particles are Microease 110S, 114S, 116 (micronized synthetic waxes), Micropoly 210, 250S (micronized polyethylene), Microslip (micronized polytetrafluoroethylene), and Microsilk (combination of polyethylene and polytetrafluoroethylene), all of which are available from Micro Powder, Inc. Other examples include Luna (smooth silica particles) particles available from Phenomenex, MP-2200 (polymethylmethacrylate), EA-209 (ethylene/acrylate copolymer), SP-501(nylon-12), ES-830 (polymethly methacrylate), BPD-800, BPD-500 (polyurethane) particles available from Kobo Products, Inc. and silicone resins sold under the name Tospearl particles by GE Silicones. Ganzpearl GS-0605 crosslinked polystyrene (available from Presperse) is also useful.

Non limiting examples of hybrid particles include Ganzpearl GSC-30SR (Sericite & crosslinked polystyrene hybrid powder), and SM-1000, SM-200 (mica and silica hybrid powder available from Presperse).

In one embodiment of the present invention, the particles used in the composition are hollow particles. In a preferred embodiment, the hollow particles are fluid-encapsulated, flexible microspheres. The microspheres are structurally hollow, however, they may contain various fluids, which encompass liquids and gases and their isomers. The gases include, but not limited to, butane, pentane, air, nitrogen, oxygen, carbon dioxide, and dimethyl ether. If used, liquids may only partially fill the microspheres. The liquids include water and any compatible solvent. The liquids may also contain vitamins, amino acids, proteins and protein derivatives, herbal extracts, pigments, dyes, antimicrobial agents, chelating agents, UV absorbers, optical brighteners, silicone compounds, perfumes, humectants which are generally water soluble, additional conditioning agents which are generally water insoluble, and mixtures thereof. In one embodiment, water soluble components are preferred encompassed material. In another embodiment, components selected from the group consisting of vitamins, amino acids, proteins, protein derivatives, herbal extracts, and mixtures thereof are preferred encompassed material. In yet another embodiment, components selected from the group consisting of vitamin E, pantothenyl ethyl ether, panthenol, Polygonum multiflori extracts, and mixtures thereof are preferred encompassed material.

The particles of the present invention can have surface charges or their surface can be modified with organic or inorganic materials such as surfactants, polymers, and inorganic materials. Particle complexes are also useful. Non-limiting examples of complexes of gas-encapsulated microspheres are DSPCS-I2™ (silica modified ethylene/methacrylate copolymer microsphere) and SPCAT-I2™ (talc modified ethylene/methacrylate copolymer microsphere). Both of these are available from Kobo Products, Inc.

The surface of the particle may be charged through a static development or with the attachment of various ionic groups directly or linked via short, long or branched alkyl groups. The surface charge can be anionic, cationic, zwitterionic or amphoteric in nature.

The wall of the particles of the present invention may be formed from a thermoplastic material. The thermoplastic material may be a polymer or copolymer of at least one monomer selected from the following groups: acrylates, methacrylates, styrene, substituted styrene, unsaturated dihalides, acrylonitriles, methacrylonitrile. The thermoplastic materials may contain amide, ester, urethane, urea, ether, carbonate, acetal, sulfide, phosphate, phosphonate ester, and siloxane linkages. The hollow particles may comprise from 1% to 60% of recurring structural units derived from vinylidene chloride, from 20% to 90% of recurring structural units derived from acrylonitrile and from 1% to 50% of recurring structural units derived from a (meth)acrylic monomer, the sum of the percentages (by weight) being equal to 100. The (meth)acrylic monomer is, for example, a methyl acrylate or methacrylate, and especially the methacrylate. Preferably, the particles are comprised of a polymer or copolymer of at least one monomer selected from expanded or non-expanded vinylidene chloride, acrylic, styrene, and (meth)acrylonitrile. More preferably, the particles are comprised of a copolymer of acrylonitrile and methacrylonitrile.

Particles comprised of polymers and copolymers obtained from esters, such as, for example, vinyl acetate or lactate, or acids, such as, for example, itaconic, citraconic, maleic or fumaric acids may also be used. See, in this regard, Japanese Patent Application No. JP-A-2-112304, the full disclosure of which is incorporated herein by reference.

Non-limiting examples of commercially available suitable particles are 551 DE (particle size range of approximately 30-50 μm and density of approximately 42 kg/m$^3$), 551 DE 20 (particle size range of approximately 15-25 μm and density of approximately 60 kg/m$^3$), 461 DE (particle size range of approximately 20-40 μm and density 60 kg/m$^3$), 551 DE 80 (particle size of approximately 50-80 μm and density of approximately 42 kg/m$^3$), 091 DE (particle size range of approximately 35-55 μm and density of approximately 30 kg/m$^3$), all of which are marketed under the trademark EXPANCEL™ by Akzo Nobel. Other examples of suitable particles for use herein are marketed under the trademarks DUALITE® and MICROPEARL™ series of microspheres from Pierce & Stevens Corporation. Particularly preferred hollow particles are 091 DE and 551DE 50. The hollow particles of the present invention exist in either dry or hydrated state. The aforesaid particles are nontoxic and non irritating to the skin.

Hollow particles that are useful in the invention can be prepared, for example, via the processes described in EP-56,219, EP-348,372, EP-486,080, EP-320,473, EP-112,807 and U.S. Pat. No. 3,615,972, the full disclosure of each of which is incorporated herein by reference.

Alternatively, the wall of the hollow particles useful in the present invention may be formed from an inorganic material. The inorganic material may be a silica, a soda-lime-borosilicate glass, a silica-alumina ceramic, or an alkali alumino silicate ceramic. Non-limiting examples of commercially available suitable low density, inorganic particles are H50/10,000 EPX (particle size range approximately 20-60 μm), S38 (particle size range approximately 15-65 μm), W-210 (particle size range approximately 1-12 μm), W-410 (particle size range approximately 1-24 μm), W-610 (particle size range approximately 1-40 μm), G-200 (particle size range approximately 1-12 μm), G-400 (particle size range approximately 1-24 μm), G-600 (particle size range approximately 1-40 μm), all of which are marketed under the trademarks 3M™ Scotchlite™ Glass Bubbles, 3M™ Zeeospheres™ ceramic microspheres, and 3M™ Z-Light Spheres™ Ceramic Microspheres. Also useful are Silica shells (average particle size 3 μm) available from KOBO Products and LUXSIL™ (3-13 μm mean diameter) available from PQ Corporation.

Preferably, the wall of the hollow particles useful in the invention are flexible. "Flexible", as used herein, means that the hollow particles are easy to compress. When pressure is reduced the hollow particles regain their original volume. The flexible hollow particles could alter their shape under an applied stress, or thermal expansion and contraction due to temperature change. Thus, the particles could expand upon heating.

The particles of the invention may be permeable or non-permeable. "Permeable", as used herein, means that they permit a liquid or gas to pass through them under given conditions. Preferably, a majority of the particles of the present invention will maintain their structural integrity during normal use of the composition. More preferably, substantially all of the particles maintain their structural integrity during normal use of the composition.

Prefered particles will also have physical properties which are not significantly affected by typical processing of the composition. Preferably, particles having melting points greater than about 70° C. are used. Still more preferably, particles having a melting point greater than 80° C. are used and most preferrably particles having melting point of greater than about 95° C. are used. As used herein, melting point would refer to the temperature at which the particle transitions to a liquid or fluid state or undergoes significant deformation or physical property changes. In addition, many of the particles of present invention are cross-linked or have a cross-linked surface membrane. These particles do not exhibit a distinct melting point. Cross-linked particles are also useful as long as they are stable under the processing and storage conditions used in the making of the present compositions.

Because of the interaction between the oppositely charged species present in the emulsion and the insoluble solid particles, essentially none of the charged particles adsorbed at the interface of the internal phase and the external phase are subject to Brownian motion. Thus, the charged particles remain dispersed and are prevented from re-agglomerating in the composition. When the composition is applied to the substrate, the charged insoluble solid particles stay dispersed on the substrate. The term "essentially none" as used herein means less than about 30%, preferably less than about 10%, more preferably less than about 5%.

Brownian motion can be observed by transmitted light microscopy according to the method set forth hereinafter in the analytical methods section.

In a preferred embodiment of the present invention, essentially all of the charged species and charged particles accumulate at the interface between the internal phase and the external phase of the emulsion. As used herein, the term "essentially all" means that at least about 70%, preferably at least about 90%, more preferably at least about 95% of the charged pigment particles are accumulated at the interface of the internal phase and the external phase of the emulsion. The accumulation of insoluble solid particles at the interface between the internal phase and the external phase of the emulsion can be observed by light and electron microscopy using the method set forth hereinafter in the Analytical Methods section.

1. Charged Pigment Particles

The charged insoluble solid particles of the present invention may comprise charged pigment particles which may be organic, inorganic, or a mixture thereof. As used herein, the term "pigment" means an insoluble solid particulate material that reflects light of certain wavelengths while absorbing light of other wavelengths, including luminescent solids. Suitable charged pigment particles include organic pigments which are generally various aromatic types including azo, indigoid, triphenylmethane, anthraquinone, and xanthine dyes which are designated as D&C and FD&C blues, browns, greens, oranges, reds, yellows, etc. Organic pigments generally consist of insoluble metallic salts of certified color additives, referred to as the Lakes. Inorganic pigments include iron oxides, titanium dioxide, ultramarine and chromium or chromium hydroxide colors, and mixtures thereof. Useful pigments include, but are not limited to, those which are extended onto inert mineral (e.g., talc, calcium carbonate, clay), or treated with silicone or other coatings (e.g., to prevent pigment particles from re-agglomerating or to change the polarity (or hydrophobicity) of the pigment.

Pigments are used to impart opacity and/or color to the compositions herein. Any pigment that is generally recognized as safe (such as those listed in C.T.F.A. Cosmetic Ingredient Handbook, 3rd Ed., Cosmetic and Fragrance Association, Inc., Washington D.C. (1982), herein incorporated by reference) can be employed in the compositions herein. Useful pigments include body pigments, inorganic white pigments, inorganic colored pigments, and pearling agents. Also useful herein are pigment and/or dye encapsulates such as nanocolorants and multi-layer interference pigments, such as Sicopearls, both from BASF. Specific examples of suitable pigments include multi-layered effects pigments, lakes, toners, mica, magnesium carbonate, calcium carbonate, magnesium silicate, aluminum magnesium silicate, silica, titanium dioxide, zinc oxide, red iron oxide, yellow iron oxide, black iron oxide, ultramarine, nylon powder, polyethylene powder, methacrylate powder, polystyrene powder, silk powder, crystalline cellulose, starch, titanated mica, iron oxide titanated mica, and bismuth oxychloride. These pigments and powders can be used independently or in combination. Titanium oxide, iron oxides, lakes, toners and mixtures thereof are especially preferred pigments for use herein.

The pigments are used in a concentration sufficient to provide a pleasing color to the composition in the container in which the cosmetic is sold and to confer the desired coverage and color to the skin when applied. Determination of the specific levels and types of pigment is within the skill of the artisan. The pigments can be used as treated particles or as the raw pigments themselves.

In order to provide a natural appearance when applied to the skin, the compositions of the present invention suitable for cosmetics will usually contain from about 0.01% to about 50%, preferably from about 1% to about 30%, most preferably from about 5% to about 20%, by weight of the composition, of charged pigment particles.

The charged pigment particles of the present invention have a primary particle size ranging from about 0.01 μm-200 μm, preferably from about 0.1 μm-100 μm, and more preferably from about 0.05 μm-90 μm. Primary particle size of the charged pigment particles can be determined by using the ASTM Designation E-20-85 "Standard Practice for Particle Size Analysis of Particulate Substances in the Range of 0.2 to 75 Micrometers by Optical Microscopy", ASTM Volume 14.02, 1993.

The relative size of the emulsion droplet to that of the charged pigment particles is unimportant so long as the charged pigment particle is not larger than the emulsion droplet. In fact, the benefits of the invention can be achieved even when the emulsion droplets and charged pigment particles form "doublets", meaning that the emulsion droplet and the charged pigment particle are of the same approximate relative size. The preferred size ratio of emulsion droplet to charged pigment particle ranges from about 1:1 to about 50:1, preferably from about 3:1 to about 30:1, most preferably from about 5:1 to about 15:1.

As herein before described, the charged pigment particles utilized in the present invention have a charge opposite to the charge of the charged species present in the emulsion. The charge of the pigment particles can be imparted by any conventional means. In a preferred embodiment of the present invention, the pigment particles contain an ionic polymer or ionic surfactant to increase or impart a charge to the pigment particles. This embodiment of the present invention is preferred not only from the standpoint of providing the most uniform coverage of the pigment on the skin, but also from the standpoint of preventing separation or "streaking" of blends of pigments in the product and on the skin. In this embodiment of the invention, the pigment particle contains an amount of ionic polymer sufficient to cover the surface of the particle without excess in bulk.

Suitable cationic polymers and anionic polymers for use herein are described herein before in section (B) entitled "The Charged Species".

The charged pigment materials are available in essentially neat, powdered form, or predispersed in various types of carriers, including but not limited to water, organic hydrophilic diluents such as lower monovalent alcohols (e.g., $C_1$-$C_4$) and low molecular weight glycols and polyols, including propylene glycol, polyethylene glycol (e.g., molecular weight 200-600 g/mole), polypropylene glycol (e.g., molecular weight 425-2025 g/mole), glycerol, butylene glycol, 1,2,4-butanetriol, sorbitol esters, 1,2,6-hexanetriol, ethanol, isopropanol, sorbitol esters, butanediol, ether propanol, ethoxylated ethers, propoxylated ethers and combinations thereof. Preferably, the charged pigment materials are predispersed in water, glycerin, butylene glycol, propylene glycol, and mixtures thereof. Examples of charged particulate materials include predispersions of ammonium polyacrylate treated $TiO_2$, butylene glycol, water, and ammonium zirconium carbonate, predispersions of chitosan (or a chitosan derivative) treated $TiO_2$ and butylene glycol, and predispersions of ammonium polyacrylate treated $TiO_2$, water, glycerin, and ammonium zirconium carbonate.

D. Optional Ingredients

The compositions herein may contain a wide variety of optional ingredients that perform one or more functions useful in products of the type described herein. Such optional ingredients may be found in either the internal phase or the external phase (or any other phase) of the compositions herein. The *CTFA Cosmetic Ingredient Handbook*, Second Edition (1992) describes a wide variety of nonlimiting cosmetic and pharmaceutical ingredients commonly used in the skin care industry, which are suitable for use in the compositions of the present invention. Examples of these ingredient classes include: abrasives, absorbents, aesthetic components such as fragrances, pigments, colorings/colorants, essential oils, skin sensates, astringents, etc.), anti-acne agents, anti-caking agents, antifoaming agents, antimicrobial agents, anti-oxidants, binders, biological additives, buffering agents, bulking agents, chelating agents, chemical additives, colorants, cosmetic astringents, cosmetic biocides, denaturants, drug astringents, external analgesics, enzymes, emulsifiers, film formers or materials, e.g., polymers, for aiding the film-forming properties and substantivity of the composition, opacifying agents, other pigments, pH adjusters, propellants, proteins, reducing agents, sequestrants, skin bleaching and lightening agents, skin-conditioning agents (e.g., humectants, including miscellaneous and occlusive), skin soothing and/or healing agents), skin treating agents, structuring agents, organic and inorganic sunscreen agents, thickeners, vitamins and derivatives thereof.

Nonlimiting examples of optional components include the following:

1. Emulsifiers

The emulsion compositions of the present invention preferably comprise from about 0.1% to about 25%, more preferably from about 0.5% to about 10%, and most preferably from about 0.5% to about 5%, by weight of the composition, of an emulsifier to help disperse and suspend the internal phase within the external phase. Emulsifiers having a hydrophilic-lipophilic balance value (HLB) ranging from about 7 to about 16 are suitable for use in the oil-in-water emulsion compositions described herein. Emulsifiers having a hydrophilic-lipophilic balance value (HLB) ranging from about 1 to about 8 are suitable for use in the water-in-oil emulsion compositions described herein. (See, Wilkinson and Moore, *Harry's Cosmeticology*, 7th Ed. 1982, p. 738, and Schick and Fowkes, Surfactant Science Series, Vol. 2, *Solvent Properties of Surfactant Solutions*, p 607.)

Emulsifiers for use herein can be selected from the group consisting of anionic, cationic, nonionic, amphoteric, and mixtures thereof. Examples of suitable emulsifiers are set forth in the C.T.F.A. Cosmetic Ingredient Handbook, 3rd Ed., Cosmetic and Fragrance Assn., Inc., Washington D.C. (1982) pp. 587-592; Remington's Pharmaceutical Sciences, 15th Ed. 1975, pp. 335-337; and Cosmetic Bench Reference, Cosmetics & Toiletries, pp. 1.22-1.25 (1996).

Polymeric ionic surfactants are especially preferred for use as the emulsifier in the oil-in-water emulsion compositions of the present invention. As used herein, the term "polymeric ionic surfactant" refers to charged amphiphilic polymers (i.e., cationic, anionic or amphoteric) which can lower surface tension. It has been found that when polymeric ionic surfactants are employed as the emulsifier in the oil-in-water emulsion compositions herein, that non-agglomeration of the particles in the product and on the substrate is maximized. This occurs when polymeric ionic surfactants are employed as the emulsifier in the oil-in-water emulsions, they coat the emulsion droplet in a manner such that both steric and electrostatic forces work to cause the particles to accumulate at the interface of the internal phase and the external phase of the emulsion. By contrast, when low molecular weight ionic surfactants are employed as the emulsifier in the oil-in-water emulsion compositions herein, they coat the emulsion droplet in a manner such that only electrostatic forces work to cause the particles to accumulate at the interface of the internal phase and the external phase of the emulsion. Likewise, when nonionic surfactants are employed, no electrostatic forces of the surfactant itself promote the accumulation of the particles at the interface of the internal phase and the external phase of the emulsion.

Cationic surfactants can desirably be employed as emulsifiers in the compositions herein. Useful cationic surfactants include, but are not limited to, alkylamines, alkyl imidazolines, ethoxylated amines, quaternary alkylbenzyldimethylammonium salts, quaternary alkyl betaines, quaternary heterocyclic ammonium salts, quaternary tetraalkylammonium salts and mixtures thereof.

Specific cationic surfactants useful herein include those disclosed in U.S. Pat. No. 5,151,209, to McCall et al., issued Sep. 29, 1992; U.S. Pat. No. 5,151,210, to Steuri et al., issued Sep. 29, 1992; U.S. Pat. No. 5,120,532, to Wells et al., issued Jun. 9, 1992; U.S. Pat. No. 4,387,090, to Bolich, issued Jun. 7, 1983; U.S. Pat. No. 3,155,591, Hilfer, issued Nov. 3, 1964; U.S. Pat. No. 3,929,678, to Laughlin et al., issued Dec. 30, 1975; U.S. Pat. No. 3,959,461, to Bailey et al., issued May 25, 1976; *McCutcheon's, Detergents & Emulsifiers*, (North American edition 1979) M.C. Publishing Co.; and Schwartz, et al., *Surface Active Agents, Their Chemistry and Technology*, New York: Interscience Publishers, 1949.

Anionic surfactants can also be used as emulsifiers in the compositions herein. Useful anionic surfactants include, but are not limited to, acylamino acids and their salts, including acylglutamates, acyl peptides, sarcosinates and taurates, carboxylic acids and their salts, including alkanoic acid and alkanoates, ester carboxylic acids and ether carboxylic acids, phosphoric acid esters and their salts, including acyl isethionates, alkylaryl sulfonates, and sulfosuccinates, and sulfuric acid esters, including alkyl ether sulfates and alkyl sulfates.

Specific anionic surfactants useful herein include those set forth in U.S. Pat. No. 3,929,678, to Laughlin et al., issued Dec. 30, 1975.

Amphoteric and zwitterionic surfactants are also useful herein. Examples of amphoteric and zwitterionic surfactants which can be used in the compositions of the present invention are those which are broadly described as derivatives of aliphatic secondary and tertiary amines in which the aliphatic radical can be straight or branched chain and wherein one of the aliphatic substituents contains from about 8 to about 22 carbon atoms (preferably $C_8$-$C_{18}$) and one contains an anionic water solubilizing group, e.g., carboxy, sulfonate, sulfate, phosphate, or phosphonate. Examples are alkyl imino acetates, and iminodialkanoates and aminoalkanoates, imidazolinium and ammonium derivatives. Other suitable amphoteric and zwitterionic surfactants are those selected from the group consisting of betaines, sultaines, hydroxysultaines, alkyl sarcosinates (e.g., $C_{12}$-$C_{30}$), and alkanoyl sarcosinates.

Nonionic surfactants can also be used in the compositions herein. Among the nonionic surfactants that are useful herein are those that can be broadly defined as condensation products of long chain alcohols, e.g. C8-30 alcohols, with sugar or starch polymers, i.e., glycosides. These compounds can be represented by the formula $(S)_n$—O—R wherein S is a sugar moiety such as glucose, fructose, mannose, and galactose; n is an integer of from about 1 to about 1000, and R is a C8-30 alkyl group. Examples of long chain alcohols from which the alkyl group can be derived include decyl alcohol, cetyl alcohol, stearyl alcohol, lauryl alcohol, myristyl alcohol, oleyl alcohol, and the like. Preferred examples of these surfactants include those wherein S is a glucose moiety, R is a C8-20 alkyl group, and n is an integer of from about 1 to about 9. Commercially available examples of these surfactants include decyl polyglucoside (available as APG 325 CS from Henkel) and lauryl polyglucoside (available as APG 600 CS and 625 CS from Henkel).

Other useful nonionic surfactants include the condensation products of alkylene oxides with fatty acids (i.e. alkylene oxide esters of fatty acids). These materials have the general formula $RCO(X)_nOH$ wherein R is a C10-30 alkyl group, X is —$OCH_2CH_2$— (i.e. derived from ethylene glycol or oxide) or —$OCH_2CHCH_3$— (i.e. derived from propylene glycol or oxide), and n is an integer from about 6 to about 200. Other nonionic surfactants are the condensation products of alkylene oxides with 2 moles of fatty acids (i.e. alkylene oxide diesters of fatty acids). These materials have the general formula $RCO(X)_nOOCR$ wherein R is a C10-30 alkyl group, X is —$OCH_2CH_2$— (i.e. derived from ethylene glycol or oxide) or —$OCH_2CHCH_3$— (i.e. derived from propylene glycol or oxide), and n is an integer from about 6 to about 100. Other nonionic surfactants are the condensation products of alkylene oxides with fatty alcohols (i.e. alkylene oxide ethers of fatty alcohols). These materials have the general formula $R(X)_nOR'$ wherein R is a C10-30 alkyl group, X is —$OCH_2CH_2$— (i.e. derived from ethylene glycol or oxide) or —$OCH_2CHCH_3$— (i.e. derived from propylene glycol or oxide), and n is an integer from about 6 to about 100 and R' is H or a C10-30 alkyl group. Still other nonionic surfactants are the condensation products of alkylene oxides with both fatty acids and fatty alcohols [i.e. wherein the polyalkylene oxide portion is esterified on one end with a fatty acid and etherified (i.e. connected via an ether linkage) on the other end with a fatty alcohol]. These materials have the general formula $RCO(X)_nOR'$ wherein R and R' are C10-30 alkyl groups, X is —$OCH_2CH_2$ (i.e. derived from ethylene glycol or oxide) or —$OCH_2CHCH_3$— (derived from propylene glycol or oxide), and n is an integer from about 6 to about 100. Nonlimiting examples of these alkylene oxide derived nonionic surfactants include ceteth-6, ceteth-10, ceteth-12, ceteareth-6, ceteareth-10, ceteareth-12, steareth-6, steareth-10, steareth-12, steareth-20, steareth-21, PEG-6, stearate, PEG-10 stearate, PEG-100 stearate, PEG-12 stearate, PEG-20 glyceryl stearate, PEG-80 glyceryl tallowate, PEG-10 glyceryl stearate, PEG-30 glyceryl cocoate, PEG-80 glyceryl cocoate, PEG-200 glyceryl tallowate, PEG-8 dilaurate, PEG-10 distearate, and mixtures thereof.

Still other useful nonionic surfactants include polyhydroxy fatty acid amide surfactants corresponding to the structural formula:

wherein: $R^1$ is H, $C_1$-$C_4$ alkyl, 2-hydroxyethyl, 2-hydroxypropyl, preferably $C_1$-$C_4$ alkyl, more preferably methyl or ethyl, most preferably methyl; $R^2$ is $C_5$-$C_{31}$ alkyl or alkenyl, preferably $C_7$-$C_{19}$ alkyl or alkenyl, more preferably $C_9$-$C_{17}$ alkyl or alkenyl, most preferably $C_{11}$-$C_{15}$ alkyl or alkenyl; and Z is a polhydroxyhydrocarbyl moiety having a linear hydrocarbyl chain with a least 3 hydroxyls directly connected to the chain, or an alkoxylated derivative (preferably ethoxylated or propoxylated) thereof. Z preferably is a sugar moiety selected from the group consisting of glucose, fructose, maltose, lactose, galactose, mannose, xylose, and mixtures thereof. An especially preferred surfactant corresponding to the above structure is coconut alkyl N-methyl glucoside amide (i.e., wherein the $R^2CO$— moiety is derived from coconut oil fatty acids). Processes for making compositions containing polyhydroxy fatty acid amides are disclosed, for example, in G.B. Patent Specification 809,060, published Feb. 18, 1959, by Thomas Hedley & Co., Ltd.; U.S. Pat. No. 2,965,576, to E. R. Wilson, issued Dec. 20, 1960; U.S. Pat. No. 2,703,798, to A. M. Schwartz, issued Mar. 8, 1955; and U.S. Pat. No. 1,985,424, to Piggott, issued Dec. 25, 1934.

Preferred among the nonionic surfactants are those selected from the group consisting of steareth-21, ceteareth-20, ceteareth-12, sucrose cocoate, steareth-100, PEG-100 stearate, and mixtures thereof.

Other nonionic surfactants suitable for use herein include sugar esters, polyesters and polyglycerol esters, alkoxylated sugar esters and polyesters, C1-C30 fatty acid esters of C1-C30 fatty alcohols, alkoxylated derivatives of C1-C30 fatty acid esters of C1-C30 fatty alcohols, alkoxylated ethers of C1-C30 fatty alcohols, polyglyceryl esters of C1-C30 fatty acids, C1-C30 esters of polyols, C1-C30 ethers of polyols, alkyl phosphates, polyoxyalkylene fatty ether phosphates, fatty acid amides, acyl lactylates, and mixtures thereof. Nonlimiting examples of these emulsifiers include: polyethylene glycol 20 sorbitan monolaurate (Polysorbate 20), polyethylene glycol 5 soya sterol, Steareth-20, Ceteareth-20, PPG-2 methyl glucose ether distearate, Ceteth-10, Polysorbate 80, cetyl phosphate, potassium cetyl phosphate, diethanolamine cetyl phosphate, Polysorbate 60, glyceryl stearate, polyoxyethylene 20 sorbitan trioleate (Polysorbate 85), sorbitan monolaurate, polyoxyethylene 4 lauryl ether sodium stearate, polyglyceryl-4 isostearate, hexyl laurate, PPG-2 methyl glucose ether distearate, PEG-100 stearate, and mixtures thereof.

Another emulsifier useful herein are fatty acid ester blends based on a mixture of sorbitan or sorbitol fatty acid ester and sucrose fatty acid ester, the fatty acid in each instance being preferably $C_8$-$C_{24}$, more preferably $C_{10}$-$C_{20}$. The preferred fatty acid ester emulsifier is a blend of sorbitan or sorbitol $C_{16}$-$C_{20}$ fatty acid ester with sucrose $C_{10}$-$C_{16}$ fatty acid ester, especially sorbitan stearate and sucrose cocoate. This is commercially available from ICI under the trade name Arlatone 2121.

Emulsions of the present invention can include a silicone containing emulsifier or surfactant. A wide variety of silicone emulsifiers are useful herein. These silicone emulsifiers are typically organically modified organopolysiloxanes, also known to those skilled in the art as silicone surfactants. Useful silicone emulsifiers include dimethicone copolyols or dimethicone copolyol crosspolymers. These materials are polydimethyl siloxanes, which may or may not be crosslinked, and have been modified to include polyether side chains or crosslinked chains such as polyethylene oxide chains, polypropylene oxide chains, mixtures of these chains, and polyether chains containing moieties derived from both ethylene oxide and propylene oxide. Other examples include alkyl-modified dimethicone copolyols, i.e., compounds which contain C2-C30 pendant side chains. Still other useful dimethicone copolyols include materials having various cationic, anionic, amphoteric, and zwitterionic pendant moieties.

The dimethicone copolyol emulsifiers useful herein can be described by the following general structure:

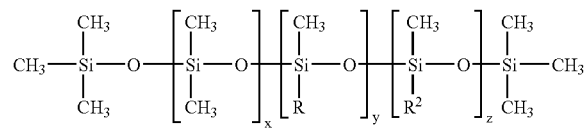

wherein R is C1-C30 straight, branched, or cyclic alkyl and $R^2$ is selected from the group consisting of $$-(CH_2)_n-O-(CH_2CHR^3O)_m-H,$$

and $$-(CH_2)_n-O-(CH_2CHR^3O)_m-(CH_2CHR^4O)_o-H,$$

wherein n is an integer from 3 to about 10; $R^3$ and $R^4$ are selected from the group consisting of H and C1-C6 straight or branched chain alkyl such that $R^3$ and $R^4$ are not simultaneously the same; and m, o, x, and y are selected such that the molecule has an overall molecular weight from about 200 to about 10,000,000, with m, o, x, and y being independently selected from integers of zero or greater such that m and o are not both simultaneously zero, and z being independently selected from integers of 1 or greater. It is recognized that positional isomers of these copolyols can be achieved. The chemical representations depicted above for the $R^2$ moieties containing the $R^3$ and $R^4$ groups are not meant to be limiting but are shown as such for convenience.

Also useful herein, although not strictly classified as dimethicone copolyols, are silicone surfactants as depicted in the structures in the previous paragraph wherein $R^2$ is:

$$-(CH_2)_n-O-R^5,$$

wherein $R^5$ is a cationic, anionic, amphoteric, or zwitterionic moiety.

Nonlimiting examples of dimethicone copolyols and other silicone surfactants useful as emulsifiers herein include polydimethylsiloxane polyether copolymers with pendant polyethylene oxide sidechains, polydimethylsiloxane polyether copolymers with pendant polypropylene oxide sidechains, polydimethylsiloxane polyether copolymers with pendant mixed polyethylene oxide and polypropylene oxide sidechains, polydimethylsiloxane polyether copolymers with pendant mixed poly(ethylene)(propylene)oxide sidechains, polydimethylsiloxane polyether copolymers with pendant organobetaine sidechains, polydimethylsiloxane polyether copolymers with pendant carboxylate sidechains, polydimethylsiloxane polyether copolymers with pendant quaternary ammonium sidechains; and also further modifications of the preceding copolymers containing pendant C2-C30 straight, branched, or cyclic alkyl moieties. Examples of commercially available dimethicone copolyols useful herein sold by Dow Corning Corporation are Dow Corning® 190, 193, Q2-5220, 2501 Wax, 2-5324 fluid, 3225C and 5225C. Cetyl dimethicone copolyol is commercially available under the tradename ABIL EM-90 or as a mixture with polyglyceryl-4 isostearate (and) hexyl laurate and is sold under the tradename ABIL® WE-09 (both available from Goldschmidt). Cetyl dimethicone copolyol is also commercially available as a mixture with hexyl laurate (and) polyglyceryl-3 oleate (and) cetyl dimethicone and is sold under the tradename ABIL® WS-08 (also available from Goldschmidt). Other nonlimiting examples of dimethicone copolyols also include lauryl dimethicone copolyol, dimethicone copolyol acetate, dimethicone copolyol adipate, dimethicone copolyolamine, dimethicone copolyol behenate, dimethicone copolyol butyl ether, dimethicone copolyol hydroxy stearate, dimethicone copolyol isostearate, dimethicone copolyol laurate, dimethicone copolyol methyl ether, dimethicone copolyol phosphate, and dimethicone copolyol stearate. See, *International Cosmetic Ingredient Dictionary*, Fifth Edition, 1993.

Dimethicone copolyol emulsifiers useful herein are described, for example, in U.S. Pat. No. 4,960,764, to Figueroa, Jr. et al., issued Oct. 2, 1990; European Patent No. EP 330,369, to SaNogueira, published Aug. 30, 1989; G. H. Dahms, et al., "New Formulation Possibilities Offered by Silicone Copolyols," *Cosmetics & Toiletries*, vol. 110, pp. 91-100, March 1995; M. E. Carlotti et al., "Optimization of W/O-S Emulsions And Study Of The Quantitative Relationships Between Ester Structure And Emulsion Properties," *J. Dispersion Science And Technology*, 13(3), 315-336 (1992); P. Hameyer, "Comparative Technological Investigations of Organic and Organosilicone Emulsifiers in Cosmetic Water-in-Oil Emulsion Preparations," HAPPI 28(4), pp. 88-128 (1991); J. Smid-Korbar et al., "Efficiency and usability of silicone surfactants in emulsions," *Provisional Communication, International Journal of Cosmetic Science*, 12, 135-139 (1990); and D. G. Krzysik et al., "A New Silicone Emulsifier For Water-in-Oil Systems," *Drug and Cosmetic Industry*, vol. 146(4) pp. 28-81 (April 1990).

2. Crosslinked Organopolysiloxane Gel Networks

The compositions of the present invention may optionally contain one or more crosslinked organopolysiloxane get networks. An example of the production of the organopolysiloxane polymer gel network powder includes the process in which an organopolysiloxane composition (i.e., additional-curable, condensation-curable, or peroxide-curable) is mixed with water in the presence of a surfactant (nonionic, anionic, cationic, or amphoteric), and, after mixing to homogeneity in a homomixer, colloid mill, homogenizer, propeller mixer, etc., this is cured by discharge into hot water (temperature at least 50° C.) and is then dried; the organopolysiloxane composition (addition-curable, condensation-curable, or peroxide-curable) is cured by spraying it directly into a heated current; the powder is obtained by curing a radiation-curable organopolysiloxane composition by spraying it under high energy radiation; the organopolysiloxane composition (addition-curable, condensation-curable, peroxide-curable) or high energy-curable organopolysiloxane composition is cured, the latter by high energy radiation, and the product is then pulverized using a known pulverizer such as, for example, a ball mill, atomizer, kneader, roll mill, etc., to thereby form the powder. Suitable organopolysiloxane polymer network powders include vinyl dimethicone/methicone silesquioxane crosspolymers like Shin-Etsu's KSP-100, KSP-101, KSP-102, KSP-103, KSP-104, KSP-105, hybrid silicone powders that contain a fluoroalkyl group like Shin-Etsu's KSP-200, and hybrid silicone powders that contain a phenyl group such as Shin-Etsu's KSP-300; and Dow Corning's DC 9506.

Preferred organopolysiloxane gel networks are dimethicone/vinyl dimethicone crosspolymers. Such dimethicone/vinyl dimethicone crosspolymers are supplied by a variety of suppliers including Dow Corning (DC 9040 and DC 9041), General Electric (SFE 839), Shin Etsu (KSG-15, 16, 18 [dimethicone/phenyl vinyl dimethicone crosspolymer] and KSG-21 [dimethicone copolyol crosspolymer]), Grant Industries (Gransil™ line of materials), lauryl dimethicone/vinyl dimethicone crosspolymers supplied by Shin Etsu (e.g., KSG-41, KSG-42, KSG-43, and KSG-44), lauryl dimethicone/dimethicone copolyol crosspolymers also supplied by Shin-Etsu (e.g., KSG-31, KSG-32, KSG-33, and KSG-34). Additional polymers from Shin-Etsu which are suitable fro use in the present invention include KSG-210, -310, 320, 330, and 340. Crosslinked organopolysiloxane polymer gel networks useful in the present invention and processes for making them are further described in U.S. Pat. No. 4,970,252 to Sakuta et al., issued Nov. 13, 1990; U.S. Pat. No. 5,760,116 to Kilgour et al., issued Jun. 2, 1998; U.S. Pat. No. 5,654,362 to Schulz, Jr. et al. issued Aug. 5, 1997; and Japanese Patent Application JP 61-18708, assigned to Pola Kasei Kogyo KK.

Another organopolysiloxane gel network that is suitable for inclusion into the presently claimed compositions is a polyethersiloxane block copolymer network comprising one or more polyether blocks, each comprising i) two or more structural units of the formula —$R^1O$— Preferred organopolysiloxane compositions are dimethicone/vinyl dimethicone crosspolymers. Such dimethicone/vinyl dimethicone crosspolymers are supplied by a variety of suppliers including Dow Corning (DC 9040 and DC 9041), General Electric (SFE 839), Shin Etsu (KSG-15, 16, 18 [dimethicone/phenyl vinyl dimethicone crosspolymer]), and Grant Industries (Gransil™ line of materials). Cross-linked organopolysiloxane elastomers useful in the present invention and processes for making them are further described in U.S. Pat. No. 4,970,252 to Sakuta et al., issued Nov. 13, 1990; U.S. Pat. No. 5,760,116 to Kilgour et al., issued Jun. 2, 1998; U.S. Pat. No. 5,654,362 to Schulz, Jr. et al. issued Aug. 5, 1997; and Japanese Patent Application JP 61-18708, assigned to Pola Kasei Kogyo KK, each of which are herein incorporated by reference in its entirety, wherein each $R^1$ is independently a divalent hydrocarbon radical or $R^2$, wherein $R^2$ is a trivalent hydrocarbon radical, and ii) one or more polysiloxane blocks, each comprising two or more structural units of the formula —$R^3{}_2SiO_{2/2}$— wherein each $R^3$ is independently a monovalent hydrocarbon radical or $R^2$, and wherein at least one polyether block of the copolymer network is bonded to at least one polysiloxane block of the copolymer network by a link according to formula

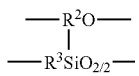

wherein the R2O unit of this formula is a unit of the at least one polyether block and the $R^2R^3SiO_{2/2}$ unit of the structure of this formula is a unit of the at least one polysiloxane unit. This copolymer network is described in further detail in copending U.S. application Ser. No. 09/592,193, filed on Jun. 12, 2000 in the name of Kilgour et al.

The present compositions comprise from about 0.1% to about 15%, by weight of the composition, of the crosslinked organopolysiloxane gel network. In preferred embodiments, the network is present in the composition in an amount of from about 2% to about 10%, by weight of the composition.

3. Waxes/Thickeners

Optionally, the compositions described herein may contain one or more cosmetically acceptable thickeners in either the oil or water phase to affect viscosity, feel, texture or stability. Examples include cellulose derivatives, organically modified clays, organic thickeners and waxes.

Waxes are lower-melting organic mixtures or compounds of high molecular weight, solid at room temperature and generally similar in composition to fats and oils except that they contain no glycerides. They can be hydrocarbons, esters of fatty acids or alcohols. Waxes useful in the present invention are selected from the group consisting of animal waxes, vegetable waxes, mineral waxes, natural waxes, synthetic waxes, petroleum waxes, ethylenic polymers, hydrocarbons, silicone waxes, and mixtures thereof.

Water and oil dispersible clays may be useful to thicken the water or the oil phase of the compositions herein. The water dispersible clays comprise bentonite and hectorite, such as Bentone EW, LT from Rheox; magnesium aluminum silicate, such as Veegum from Vanderbilt Co., attapulgite such as Attasorb or Pharmasorb from Engelhard, Inc.; laponite and montmorrilonite, such as Gelwhite from ECC America, and mixtures thereof. The oil dispersible clays include quaternium-18 bentonite, such as Bentone 34 and 38 from Rheox; the Claytone Series from ECC America; quaternium-18 hectorite, such as Bentone gels from Rheox; and mixtures thereof. Other particulate or organic thickeners may also be used provided they do not compromise the function or aesthetics of the foundation.

4. Structuring Agents

The compositions herein may contain a structuring agent. Without being limited by theory, it is believed that the structuring agent assists in providing rheological characteristics to the composition which contribute to the stability of the composition. For example, the structuring agent tends to assist in the formation of a liquid crystalline gel network structures. The structuring agent may also function as an emulsifier or surfactant. Preferred compositions of this invention comprise from about 1% to about 20%, more preferably from about 1% to about 10%, most preferably from about 2% to about 9%, of one or more structuring agents.

Preferred structuring agents are those having an HLB of from about 1 to about 8 and having a melting point of at least about 45° C. Suitable structuring agents are those selected from the group consisting of saturated $C_{14}$ to $C_{30}$ fatty alcohols, saturated $C_{16}$ to $C_{30}$ fatty alcohols containing from about 1 to about 5 moles of ethylene oxide, saturated $C_{16}$ to $C_{30}$ diols, saturated $C_{16}$ to $C_{30}$ monoglycerol ethers, saturated $C_{16}$ to $C_{30}$ hydroxy fatty acids, $C_{14}$ to $C_{30}$ hydroxylated and nonhydroxylated saturated fatty acids, $C_{14}$ to $C_{30}$ saturated ethoxylated fatty acids, amines and alcohols containing from about 1 to about 5 moles of ethylene oxide diols, $C_{14}$ to $C_{30}$ saturated glyceryl mono esters with a monoglyceride content of at least 40%, $C_{14}$ to $C_{30}$ saturated polyglycerol esters having from about 1 to about 3 alkyl group and from about 2 to about 3 saturated glycerol units, $C_{14}$ to $C_{30}$ glyceryl mono ethers, $C_{14}$ to $C_{30}$ sorbitan mono/diesters, $C_{14}$ to $C_{30}$ saturated ethoxylated sorbitan mono/diesters with about 1 to about 5 moles of ethylene oxide, $C_{14}$ to $C_{30}$ saturated methyl glucoside esters, $C_{14}$ to $C_{30}$ saturated sucrose mono/diesters, $C_{14}$ to $C_{30}$ saturated ethoxylated methyl glucoside esters with about 1 to about 5 moles of ethylene oxide, $C_{14}$ to $C_{30}$ saturated polyglucosides having an average of between 1 to 2 glucose units and mixtures thereof, having a melting point of at least about 45° C.

The preferred structuring agents for the oil-in-water emulsion compositions of the present invention are selected from the group consisting of stearic acid, palmitic acid, stearyl alcohol, cetyl alcohol, behenyl alcohol, stearic acid, palmitic acid, the polyethylene glycol ether of stearyl alcohol having an average of about 1 to about 5 ethylene oxide units, the polyethylene glycol ether of cetyl alcohol having an average of about 1 to about 5 ethylene oxide units, and mixtures thereof. More preferred structuring agents for use in the oil-in-water emulsion compositions of the present invention are selected from the group consisting of stearyl alcohol, cetyl alcohol, behenyl alcohol, the polyethylene glycol ether of stearyl alcohol having an average of about 2 ethylene oxide units (steareth-2), the polyethylene glycol ether of cetyl alcohol having an average of about 2 ethylene oxide units, and mixtures thereof. Even more preferred structuring agents for the oil-in-water emulsion compositions are those selected from the group consisting of stearic acid, palmitic acid, stearyl alcohol, cetyl alcohol, behenyl alcohol, steareth-2, and mixtures thereof.

5. Uncharged Insoluble Solid Particles

The compositions of the present invention may optionally comprise from about 0.1% to about 20%, preferably from about 1% to about 15%, and more preferably from about 1% to about 10%, by weight of the composition, of insoluble solid particles such as those hereinbefore described with the exception that these are not charged.

6. Water-Soluble Skin Conditioning Ingredients

Preferred compositions of the invention can also comprise a water soluble skin conditioning component comprising one or more water soluble skin conditioning compounds. The water soluble skin conditioning component is useful for lubricating the skin, increasing the smoothness and suppleness of the skin, preventing or relieving dryness of the skin, hydrating the skin, and/or protecting the skin. The skin conditioning component enhances the skin appearance improvements of the present invention, including but not limited to essentially immediate visual improvements in skin appearance. The water soluble skin conditioning component is preferably selected from the group consisting of humectants, moisturizers and mixtures thereof. The water soluble skin conditioning component is preferably present at a level of at least about 0.1%, more preferably from about 1% to about 50%, still more preferably from about 2% to about 30% and most preferably from about 5% to about 25% (e.g., about 5% to about 15%).

Nonlimiting examples of water soluble conditioning compounds include those selected from the group consisting of polyhydric alcohols, polypropylene glycols, dipropylene glycol, polyethylene glycols, ureas, pyrolidone carboxylic acids, ethoxylated and/or propoxylated C3-C6 diols and triols, alpha-hydroxy C2-C6 carboxylic acids, ethoxylated and/or propoxylated sugars, sugars having up to about 12 carbons atoms, sugar alcohols having up to about 12 carbon atoms, and mixtures thereof. Specific examples of useful water soluble conditioning agents include materials such as urea; guanidine; glycolic acid and glycolate salts (e.g. ammonium and quaternary alkyl ammonium); lactic acid and lactate salts (e.g. ammonium and quaternary alkyl ammonium); sucrose, fructose, glucose, eruthrose, erythritol, sorbitol, hydroxypropyl sorbitol, mannitol, glycerol, hexane triol, propylene glycol, butylene glycol, hexylene glycol, threitol, pentaerythritol, xylitol, glucitol, and the like; polyethylene glycols such as PEG-2, PEG-3, PEG-30, PEG-50, polypropylene glycols such as PPG-9, PPG-12, PPG-15, PPG-17, PPG-20, PPG-26, PPG-30, PPG-34; alkoxylated glucose; hyaluronic acid; and mixtures thereof. Also useful are materials such as aloe vera in any of its variety of forms (e.g., aloe vera gel); lactamide monoethanolamine; acetamide monoethanolamine; panthenol; and mixtures thereof. Also useful are ethoxylated glycerols and propoxylated glycerols as described in U.S. Pat. No. 4,976,953, to Orr et al., issued Dec. 11, 1990. Other skin conditioning agents are listed in the Cosmetic Bench Reference, Cosmetics & Toiletries, p. 1.34 (1996).

7. Skin Active Ingredients

Various skin active ingredients can also optionally and desirably be employed in the compositions of the present invention. As used herein, "skin active agents" are cosmetically acceptable materials for application onto human skin, and which provide a therapeutic or prophylactic health or appearance benefit to the skin. For example, such actives may provide anti-acne activity, anti-wrinkling activity, topical anesthetic activity, topical antibacterial activity, topical anti-inflammatory activity, artificial tanning or acceleration, antimicrobial activity, antifungal activity, sun protection, or combinations thereof, upon topical application onto human skin.

The term "safe and effective amount" as used herein, means an amount of a skin care active ingredient high enough to modify the condition to be treated or to deliver the desired skin benefit, but low enough to avoid serious side effects, at a reasonable benefit to risk ratio within the scope of sound medical judgment. What is a safe and effective amount of the active ingredient will vary with the specific active, the ability of the active to penetrate through the skin, the age, health condition, and skin condition of the user, and other like factors.

By "cosmetically acceptable" is meant that the ingredient is suitable for use in contact with the skin of humans and other animals without undue toxicity, incompatibility, instability, irritation, allergic response and the like.

Typically, these actives of the present invention comprise from about 0.001% to about 20%, preferably from about 0.01% to about 10%, and more preferably from about 0.025% to about 5%, by weight of the composition.

The actives useful herein can be categorized by their therapeutic/prophylactic benefit or their postulated mode of action. It is, however, to be understood that the actives useful herein can in some instances provide more than one therapeutic and/or prophylactic benefits or operate via more than one mode of action. Therefore, classifications herein are made for the sake of convenience and are not intended to limit the active to that particular application or applications listed. Also, pharmaceutically-acceptable salts of these materials are useful herein.

Nonlimiting examples of skin care actives useful in the present invention include actives for preventing or reducing acne, wrinkles, lines, atrophy, inflammation, as well as topical anesthetics, artificial tanning agents and accelerators, antimicrobial agents, antifungal actives, and sunscreening actives. A wide variety of such actives are known in the art and are suitable for use herein. For example, such actives are disclosed in copending U.S. application Ser. No. 09/439,438.

In different exemplary embodiments, the skin care actives are selected from peptides (e.g., Matrixyl™ [pentapeptide derivative]), farnesol, bisabolol, phytantriol, glycerol, urea, guanidine (e.g., amino guanidine); vitamins and derivatives thereof such ascorbic acid, vitamin A (e.g., retinoid derivatives such as retinyl palmitate or retinyl proprionate), vitamin E (e.g., tocopherol acetate), vitamin $B_3$ (e.g., niacinamide) and vitamin $B_5$ (e.g., panthenol) and the like and mixtures thereof, wax-based synthetic peptides (e.g., octyl palmitate and tribehenin and sorbitan isostearate and palmitoyl-oligppeptide), anti-acne medicaments (resorcinol, salicylic acid, and the like; antioxidants (e.g., phytosterols, lipoic acid); flavonoids (e.g., isoflavones, phytoestrogens); skin soothing and healing agents such as aloe vera extract, allantoin and the like; chelators and sequestrants; and agents suitable for aesthetic purposes such as essential oils, fragrances, skin sensates, opacifiers, aromatic compounds (e.g., clove oil, menthol, camphor, eucalyptus oil, and eugenol). desquamatory actives, anti-acne actives, vitamin $B_3$ compounds, anti-oxidants, peptides, hydroxy acids, anti-oxidants, radical scavengers, chelators, farnesol, anti-inflammatory agents, topical anesthetics, tanning actives, skin lightening agents, anti-cellulite agents, flavonoids, antimicrobial actives, antifungal actives, sunscreen actives, conditioning agents, structuring agents, thickening agents, and combinations thereof. Other additional ingredients are disclosed in U.S. Pat. No. 5,011,681, to Ciotti et al., issued Apr. 30, 1991 and U.S. Pat. No. 5,939,082, to Oblong et al., issued Aug. 17, 1999, both of which are herein incorporated by reference. The above-mentioned vitamin $B_3$ compounds can be incorporated as recrystallized crystals that remain in crystalized form in the composition or as partially solubilize crystals (i.e., some of the crystals are dissolved and some remain in crystalline form in the composition.).

8. Film Forming Agents

Film forming agents may be optionally included in the compositions of the present invention to aid film substantivity and adhesion to the skin. Improving the long wear and non-transfer performance of the present compositions is quite desirable. Water-soluble, water insoluble, and water dispersible film forming agents can be used in the internal and external phases of the present compositions to give the desired end benefit.

Suitable film forming agents include organic silicone resins, fluorinated silicone resins, copolymers of organic silicone resins, e.g., trimethylsiloxysilicate from GE (SR1000), GE's copolymers of silicone resins, e.g., SF1318 (silicone resin and an organic ester of isostearic acid copolymer) and CF1301 (silicone resin and alpha methyl styrene copolymer), Dow Corning's pressure sensitive adhesives—copolymers of silicone resins and various PDMS's (BIO-PSA series); and acrylic and methacrylic polymers and resins, silicone-acrylate type copolymers and fluorinated versions of, including—silicones plus polymer SA70 from 3M, KP545 from Shin-Etsu, alkyl-acrylate copolymers, e.g., KP 561 and 562 from Shin-Etsu. Other suitable film forming polymers include:

1) decene/butene copolymer from Collaborative Labs;
2) polyvinyl based materials, e.g., PVP, PVP/VA, including Antaron/Ganex from ISP (PVP/Triacontene copolymer), Luviskol materials from BASF;
3) polyurethanes, e.g., the Polyderm series from Alzo including but not limited to Polyderm PE/PA, Polyderm PPI-SI-WS, Polyderm PPI-GH, Luviset P.U.R. from BASF;
4) polyquaternium materials, e.g., Luviquat series from BASF
5) acrylates copolymers and acrylates/acrylamide copolymers, e.g., Luvimer and Ultrahold series, both available from BASF;
6) styrene based materials; and
7) chitosan and chitosan based materials including cellulose and cellulose-based materials.

Such film formers are disclosed for example in the International Cosmetic Ingredient Dictionary and Handbook, Seventh Edition, Vol 2, 1636-1638.

II. Process for Preparing Compositions Herein

The compositions of the present invention can be generally prepared by conventional methods such as are known in the art of making cosmetic compositions. Such methods typically involve mixing of the ingredients in one or more steps to a relatively uniform state, with or without heating, cooling, application of vacuum, and the like.

The charged species can be incorporated into the composition by any conventional means. One or more of the components described herein before can be mixed together with the charged insoluble solid particles via conventional methods in any sequence. Typically, the charged or uncharged particles are dispersed in the water phase. To induce a charge on particles, one typically disperses the particles in a polar solvent. The surface charge of the particles can be adjusted by pH or by the addition of a charged species that irreversibly adsorbs at the solvent/particle interface. The dispersion is milled or mixed at high shear until the desired particle size is achieved. See e.g., Everett, D. H., *Basic Principles of Colloid Science*, Royal Society of Chemistry, Picadilly London, 1988; Lieberman, Herbert A., Rieger, Martin M., and Banker, Gilbert S., Eds., *Pharmaceutical Dosage Forms: Disperse Systems*, Vol. 1, $2^{nd}$ Ed., Marcel Dekker, Inc., New York, 1996 (pp 35-43). The emulsion is formed by slow addition of the internal phase to the external phase with high shear mechanical mixing. The charged species, polyanion, polycation or ionic surfactant, is typically added after the emulsion is formed or incorporated into the oil phase and added during emulsification. Both processes achieve the desired result. Although these are the preferred methods, one is not limited to these processes for incorporating the charged species into the composition in order to achieve the desired result.

III. Methods for Maximizing Coverage While Providing a Natural Appearance to the Skin The compositions of the present invention are useful for providing good coverage to the skin (e.g., minimizing fine lines and wrinkles and covering blemishes or irregularities in pigmentation), while at the same time providing a natural appearance to the skin (avoiding a cakey appearance).

A wide range of quantities of the compositions of the present invention can be applied to the skin to achieve these advantages. Quantities of the present compositions which are frequently applied per application are, in mg composition/$cm^2$ skin, from about 0.5 to about 3 mg/$cm^2$. Typically applications would be on the order of about once per day.

ANALYTICAL METHODS

A. Observation of Particles Accumulated at the Interface of the Internal Phase and the External Phase of the Emulsion 1. Light Microscopy Technique Equipment/Materials Nikon Microphot-SA, equipped with Differential Interference Contrast (DIC) filters
Nikon PLAN 100/1.25 oil DIC objective
Eyepiece-CFUWIN 10×/26.5
Sony 3CCD video camera
Sony monitor
Sony Color Video Printer Mavigraph UP525OMD
Corning No. 1 22 mm sq. cover slips
Rite-on microscope slides 25×75 mm, thickness 0.93 to 1.05 mm
Type A immersion oil Sample Preparation 1. Apply a small sample of product (approximately 1 gram) to the Rite-on microscope slide. Dilute the sample by applying one drop of the external phase (e.g., in a water-in-oil emulsion, water is the dilutent) of the emulsion to the top of the sample once the sample has been applied to the microscope slide.
2. Place a microscope cover on top of the sample and apply a drop of immersion oil to the top of this cover.
3. Study the sample using a Nikon Microphot-SA (or equivalent) microscope equipped with a 100× oil immersion lens, 10× oculars and DIC. Observe whether the pigment particles appear to be accumulated at the interface of the emulsion droplet. If they appear to be accumulated at the interface, proceed with Cryo-Scanning Electron Microscopy method set forth hereinbelow.

2. Cryo-Scanning Electron Microscopy Technique a) In-product Analysis

1. Place a small amount of sample in the well of a gold or copper specimen holder.
2. Rapidly plunge the sample and holder into liquid ethane cooled by a bath of liquid nitrogen.
3. Transfer the resulting solid specimen into a cryo-storage vial and store in liquid nitrogen. Note: After freezing, all samples are handled under liquid nitrogen, in a cold nitrogen gas atmosphere, or under vacuum to prevent ice crystal growth in the sample or frost formation on the sample surface.
4. Transfer the specimen into the vacuum of an Oxford CT1500 HF Cryo-preparation chamber attached to a Hitachi S4500-I Field-Emission Scanning Electron Microscope (SEM) or its equivalent.
5. Cleave or fracture the specimen under vacuum using a sharp probe to initiate the fracture plane so that a surface is created from the internal structure of the product.
6. After fracture, sublimination of the solvent (normally water) from the exposed fracture surface (etching) may be conducted to expose additional internal structure (e.g., pigments within the internal water phase). Etched structures should be compared with non-etched structures to identify potential artifacts.
7. Using a Denton Planar Magnetron Sputtering Head or its equivalent, coat the sample at −120° C. with a thin film (~2 nm) of Au/Pd to enhance contrast and reduce specimen charge-up.
8. Transfer the sample onto the cold storage inside the SEM and analyze at −110° C. using the upper (high-resolution) detector at 1.5 keV beam acceleration voltage for imaging, and at 10-20 keV for element identification by x-ray analysis. X-ray analysis may be conducted at a single point or an x-ray elemental image may be formed. X-ray analysis is performed with an Isis Energy Dispersive Spectrometer, or its equivalent, with a thin window silicon detector.
9. Observe whether the particles appear to be accumulated at the interface of the emulsion droplet. This method can be done definitively by comparing three types of emulsion droplet fractures. The first and most common fracture is a cross-fracture where the fracture plane passes through the cross section of an emulsion droplet. In a cosmetic composition containing pigment particles, these particles can readily be imaged and x-ray mapped around the circumference of the droplet. The other two fractures result from the fracture plane propagating around the surface of the droplet either between the droplet and the pigment particles or between the pigment particles and the bulk phase. In the first case, the pigment particles will be seen lining the depression created by the droplets in the bulk phase (i.e., the negative replica). In the second case, pigment particles will be seen over the surface of the droplet protruding from the bulk phase (i.e., the positive replica). The collaboration of these three tests is definitive.

B. Observation of Brownian Motion of the Particles

| | | | | | |
|---|---|---|---|---|---|
| A | dimethicone copolyol (10%)/cyclomethicone (90%) | 15.00 | 15.10 | 15.00 | 15.00 |
| A | Quaternium 80 (cationic) | 0.50 | — | 0.50 | — |
| A | anionic surfactant | — | — | — | 0.65 |
| A | isononyl isononanoate | 3.00 | 1.50 | 3.00 | 3.00 |
| A | sucrose ester fatty acid cottonate | 1.00 | 1.50 | — | — |
| A | propylparaben | — | 0.25 | — | — |
| B | water | 38.54 | 44.91 | 40.92 | 27.20 |

-continued

| | | | | | |
|---|---|---|---|---|---|
| B | yellow iron oxide | 1.13 | 1.13 | 1.80 | 1.30 |
| B | red iron oxide | 0.18 | 0.26 | 0.28 | 0.25 |
| B | black iron oxide | 0.15 | 0.15 | 0.09 | 0.12 |
| B | charged pigment particles: glycerin (30%), water (30%), titanium dioxide (39.5%), ammonium polyacrylate (0.1%, ammonium Zr carbonate (0.05%) | 7.90 | 7.90 | — | — |
| B | charged pigment particles: glycerin (12.5%), water (12.5%), titanium dioxide (75%), ammonium polyacrylate (0.1%, ammonium Zr carbonate (0.05%) | 5.40 | 5.40 | — | — |
| B | charged pigment particles: glycerin (25%), water (25%), titanium dioxide (49.5%), ammonium polyacrylate (0.10%), ammonium zirconium carbonate (0.05%) | 6.00 | 6.00 | — | — |
| B | charged pigment particles: butylene glycol (32.5%), water (32.85%), titanium dioxide (34.49%), ammonium polyacrylate (0.10%), ammonium zirconium carbonate (0.06%) | 8.80 | | | |
| B | rutile titanium dioxide | — | — | 8.25 | 8.25 |
| B | hydroxypropyl chitosan | — | — | — | 12.50 |

Using the equipment and procedure hereinbefore described in Analytical Method A, Observation of Particles Accumulated at the Interface of the Internal Phase and the External Phase of the Emulsion—Light Microscopy Technique, prepare a sample and observe under the microscope. If the particles appear to be attached to the surface of the emulsion droplet and appear to be stationary, proceed with Cryo-Scanning Electron Microscopy Technique set forth hereinabove. If the particles appear to be attached to the surface of the emulsion droplet using the Cryo-Scanning Electron Microscopy and appear to be stationary using the Light Microscopy Technique, there is no Brownian motion.

C. Particle Size of Emulsion Droplets

1. Particle Size of Individual Particles

Using the equipment and procedure hereinbefore described in Analytical Method A, prepare a sample and observe under the microscope. Emulsion droplet size can be measured by calibrating the level of magnification with an objective micrometer. As used herein, particle size is the average particle size of a representative sample of the product.

2. Particle Size Distribution

SEM can be used for qualitative comparisons among samples wherein the particle size of the particles varies substantially. First, select an appropriate magnification based on the particle size and the precision required. Particle size precision is limited to the size of a single image pixel. Therefore, the magnification must be high enough so the size of a single pixel is equal to or less than the precision required for the measurement. If a large range of particle size exists, several magnifications will be required to cover overlapping regions of the particle size range. Random sampling of fields-of-view is the most desirable method, however, known artifactual regions must be excluded. Ideally, the entire sample will be observed prior to selecting representative regions for measurement. The calibrated scale bar of the microscope is used as a reference for either manual or computer-aided measurement of the particles.

EXAMPLES

Examples 1-4 are nonlimiting examples of water-in-silicone liquid foundation compositions of the present invention:

| Part | Ingredient | Example 1 (wt %) | Example 2 (wt %) | Example 3 (wt. %) | Example 4 (wt. %) |
|---|---|---|---|---|---|
| A | cyclomethicone | 5.00 | 8.60 | 20.00 | 19.86 |
| B | methylparaben | 0.12 | 0.2 | 0.12 | 0.12 |
| B | carboxymethyl-cellulose | — | — | 0.29 | — |
| B | butylene glycol | — | 2.00 | — | — |
| B | moisturizer | 1.50 | 1.50 | 6.00 | 6.00 |
| B | phenoxyethanol | — | 0.30 | — | — |
| C | laureth-7 | 0.50 | — | 0.50 | 0.50 |
| C | propylparaben | 0.25 | — | 0.25 | 0.25 |
| C | sucrose ester fatty acid behenate | — | 1.5 | — | — |
| C | ozokerite wax | — | 1.5 | — | — |
| D | cationic premix (30% quaternium 80, 10% dimethicone copolyol*, 60% cyclomethicone) | 1.00 | — | — | — |
| E | dimethicone copolymer | 3.00 | — | 3.00 | 5.00 |
| G | silica | 1.00 | — | — | — |
| G | ethylene/acrylic acid copolymer | 1.00 | — | — | — |
| H | fragrance | 0.03 | — | — | — |
| H | other minor ingredients | — | — | — | — |
| | Total | 100.00 | 100.00 | 100.00 | 100.00 |

*dimethicone copolyol (10%)/cyclomethicone (90%)

Examples 1-4 are prepared as follows:

Example 1

Premixes: Mix the Part A components together and mill with a Silverson L4RT mixer equipped with a 2" emulsor screen 2000-3000 rpms for 5 minutes. Separately mix the Part B components together and mill for 30 minutes at 9000 rpms, using a Silverson L4RT mixer equipped with a 1" disintegrating screen. Separately mix the Part C components together and mix by hand until the paraben is dissolved. Separately, mix the Part D components together by hand in a beaker until uniform.

Compounding: Add Part C to Part A and mix at 3000-4000 rpms using a Silverson L4RT mixer equipped with a 2" emulsor screen for about 5 minutes. Slowly add Part B while mixing at about 6000 rpms using same Silverson setup. Total addition time should be about 10-15 minutes; the temperature should be kept at greater than about 35° C. to about 60° C. Mill the resulting mixture for about 5 minutes, maintaining good turnover. Add Part D and mill at about 6000-8000 rpms until uniform, for about 5 minutes. Add Part E, G and H and mill at 6000-8000 rpms for an additional 10 minutes, to finish product.

Example 2

Premixes: Combine the methyl paraben and butylene glycol and mix by hand until the paraben is dissolved. Add the remaining Part B components and mill on a Silverson L4RT equipped with a 1" disintegrating screen at 9000 rpms for about 30 minutes. Separately mix the Part A components and mill on a Silverson equipped with a 2": emulsor screen at 2000-3000 rpms until well mixed. Separately mix the Part C components together heat to 80° C. until melted.

Compounding: Slowly add Part B to Part A over a period of 5-10 minutes, while mixing at 6000 rpms using the Silverson equipped with a 2" emulsor screen. Transfer to a low shear mixer ~300-800 rpms (e.g., Caframo, propeller blade). Heat to 80° C. Add Part C, at about 80° C., and mix for about 5 minutes at that temperature. Cool to about room temperature while continuing to mix, to finish product.

Example 3

Prepare as for Example 1, except that no Part D, G or H are added.

Example 4

Prepare as described for Example 3.

The pigment in these foundation compositions is uniformly distributed throughout the foundation composition. When these compositions are applied to the skin, the pigment will be distributed uniformly on the skin and a natural appearance for the skin will be provided.

Examples 5-7 are oil-in-water liquid foundation compositions of the present invention.

| Part | Ingredient | Example 5 (wt %) | Example 6 (wt %) | Example 7 (wt. %) |
|---|---|---|---|---|
| A | cyclomethicone | — | 23.74 | 38.00 |
| A | silicone fluid | — | 5.92 | — |
| A | propylparaben | — | 0.25 | 0.25 |
| A | fragrance | — | 0.03 | 0.03 |
| A | polyoxyethylenesorbitan monolaurate | 8.75 | — | — |
| A | sorbitan monostearate | 3.75 | — | — |
| A | methylparaben | 0.12 | — | — |
| A | water | 12.38 | — | — |
| B | cyclomethicone | 17.47 | — | — |
| B | sucrose ester fatty acid cottonate | 2.00 | — | — |
| B | sucrose monooleate | — | — | 2.50 |
| B | glycerin | — | 1.00 | 1.00 |
| B | polyoxyethylene (23) lauryl ether | — | 0.25 | — |
| B | water | — | 14.39 | 13.75 |
| B | methylparaben | — | 0.12 | 0.12 |

-continued

| Part | Ingredient | Example 5 (wt %) | Example 6 (wt %) | Example 7 (wt. %) |
|---|---|---|---|---|
| B | titanium dioxide dispersed in silicone fluid (75% dispersion) | 3.00 | — | — |
| B | fragrance | 0.03 | — | — |
| B | propylparaben | 0.25 | — | — |
| B | isononyl isononanoate | 1.25 | — | — |
| B | dimethicone copolyol | 0.5 | — | — |
| B | trimethlsilyamodimethicone | 0.5 | — | — |
| C | Quaternium 80 (cationic) | — | 0.25 | 0.25 |
| C | ethylene/acrylic acid copolymer | — | 4.00 | — |
| C | charged pigment particles: butylene glycol (32.5%), water (32.85%), titanium dioxide (34.5%), ammonium polyacrylate (0.10%), ammonium zirconium carbonate (0.06%) | 22.86 | | |
| C | glycerin | 1.50 | — | — |
| C | yellow iron oxide | 0.95 | — | — |
| C | red iron oxide | 0.22 | — | — |
| C | black iron oxide | 0.11 | — | — |
| C | water | 20.36 | — | — |
| D | yellow iron oxide | — | 0.95 | 0.57 |
| D | red iron oxide | — | 0.28 | 0.21 |
| D | black iron oxide | — | 0.10 | 0.08 |
| D | water | — | 24.46 | 20.03 |
| D | charged pigment particles: butylene glycol (28%), water (28%), titanium dioxide (43.5%), ammonium polyacrylate (0.10%), ammonium Zr carbonate (0.06%) | — | 23.26 | — |
| D | charged pigment particles: glycerin (30%), water (30%), titanium dioxide (39.5%), ammonium polyacrylate (0.1%, ammonium Zr carbonate (0.05%) | — | — | — |
| D | charged pigment particles: glycerin (12.5%), water (12.5%), Titanium dioxide (75%), ammonium polyacrylate (0.1%, ammonium Zr carbonate (0.05%) | — | — | — |
| D | charged pigment particles: butylene glycol (32.5%), water (32.85%), titanium dioxide (34.5%), ammonium polyacrylate (0.10%), ammonium zirconium carbonate (0.06%) | — | — | 21.21 |
| D | rutile titanium dioxide | — | — | 2.00 |
| D | ethylene acrylates copolymer | 4.00 | — | — |
| E | hydroxypropylcellulose | — | 1.00 | — |
| | Total | 100.00 | 100.00 | 100.00 |

Examples 5-7 are prepared as follows:

Example 5

Premixes: Combine Part C components and mill at 9000 rpms for 30 minutes using a Silverson L4RT equipped with a 1" disintegrating screen. Separately mix the Part B ingredients together and stir for 10 minutes at 6000 rpms using Silverson L4RT equipped with a 2" emulsor screen. Separately mix the Part A components together, heat to 45-60C. and stir for 20 minutes at 1000 rpms on a Silverson L4RT equipped with a 2" emulsor screen (to form a white paste containing liquid crystals as viewed under a microscope).

Compounding: Slowly add Part B to Part A at 10 ml/minute at 1000 rpm with a Silverson 2" emulsor screen. Add Part C at 20 ml/minute at 3000 rpm with a Silverson 2" emulsor screen. Add Part D. If needed, continue mixing to obtain desired emulsion size, e.g., about 3 additional minutes at 8000 rpm with a Silverson 2" emulsor screen.

Example 6

Premixes: Combine Part D components and mix at 9000 rpm for 30 minutes using a Silverson L4RT equipped with a 1" disintegrating screen. Combine Part C ingredient/s. Combine Part B ingredients, heat to 45-60C. and mix until uniformly dissolved. Combine the Part A components, heat to 60-70° C. and mix using a stirring bar until dissolved.

Compounding: Slowly add Part A to Part B with a pipette over about 10 minutes, with mixing at 5000 rpms with a Silverson equipped with a 2" emulsor screen, and maintaining the temperature at about 60-74° C. Cool to about 30-35° C. Add Part C to the mixture and stir the mixture at 5000 rpm for 2 minutes with the Silverson 2" emulsor screen. Heat to 60C. while mixing. Slowly add Part D at 5000 rpm with the Silverson 2" emulsor head. While adding, cool to 30-35C. Add Part E and stir for 10 minutes at 5000 rpm on the Silverson 2" emulsor head. If needed, continue mixing to obtain desired emulsion size, e.g., about 3 additional minutes at 8000 rpm with a Silverson 2" emulsor screen.

Example 7

Prepare like Example 6 except that no Phase E is added.

Examples 8-10 are non limiting examples of water-in-oil solid emulsion foundations of the present invention.

| Part | Ingredient | Example 8 (wt %) | Example 9 (wt %) | Example 10 (wt %) |
| --- | --- | --- | --- | --- |
| A | cyclomethicone | 22.13 | 26.16 | 6.50 |
| A | cyclo/dimethicone copolyol | 14.49 | 10.00 | 20.0 |
| A | isononyl isononanoate | 3.0 | 3.0 | 3.0 |
| A | Abil Quat 3272 (Quaternium 80) | 1.0 | 1.0 | 0.5 |
| B | Laureth-7 | 0.5 | 0.5 | 0.5 |
| B | propylparaben | 0.25 | 0.25 | 0.25 |
| B | ethylene brassylate | 0.03 | 0.0 | 0.03 |
| C | charged pigment particles (39.5% titanium oxide, 30.0% glycerin, 30.35% water, 0.1% ammonium polyacrylate, 0.05% ammonium zirconium carbonate) | 7.9 | 7.9 | 7.9 |
| C | charged pigment particles (74.5% titanium oxide, 12.5% glycerin, 12.85% water, 0.10% ammonium polyacrylate, 0.05% ammonium zirconium carbonate) | 9.4 | 9.4 | 5.4 |
| C | charged pigment particles (49.5% titanium oxide, 25% glycerin, 23.35% water, 0.10% ammonium polyacrylate, 0.05% ammonium zirconium carbonate) | 6.0 | 6.0 | 6.0 |
| C | yellow iron oxide | 0.96 | 1.3 | 1.13 |
| C | red iron oxide | 0.70 | 0.25 | 0.18 |
| C | black iron oxide | 0.18 | 0.12 | 0.15 |
| C | methylparaben | 0.12 | 0.12 | 0.12 |
| C | water | 20.50 | 23.00 | 35.84 |
| D | dimethicone treated talc | 3.0 | 0.0 | 0.0 |
| D | polytrap | 1.34 | 3.0 | 0.0 |
| D | nontreated talc | 0.0 | 2.0 | 0.0 |
| D | ethylene acrylic acid copolymer | 2.0 | 2.0 | 2.0 |
| D | PVP K-30 (17% mix with water) | 3.0 | 0.0 | 0.0 |
| F | Ozokerite wax | 3.5 | 4.0 | 5.0 |
| F | silicone wax | 0.0 | 0.0 | 4.0 |
| | Total | 100.00 | 100.00 | 100.00 |

Examples 8-10 are silicone in water compositions and are prepared as follows:

Premixes: Combine the Part A ingredients and mix with a Silverson L4RT equipped with a 2" emulsor screen at 3000 rpm until ingredients are visibly homogeneous. Separately mix the Part B components until the paraben is essentially dissolved. Separately combine and mix the Part C ingredients using a Silverson L4RT mill at high speed (9000-10,000 rpm) using a 1" disintegrating screen for at least 30 minutes.

Compounding: Add Part B to Part A and mix at 3000-4000 rpm using a Silverson L4RT equipped with a 2" emulsor screen. Slowly add Part C and mix with the Silverson 2" emulsor screen at about 6000 rpm over a time period of about 10-15 minutes. Mill maintaining a good turnover, about 10 minutes. Add Part D components mill for an additional 5 minutes (when used, heat the PVP K-30 to 80° C. until melted and cool to 30° C. prior to addition). Heat to 80° C. and add Part F components, mix until uniform, remove air and package.

What is claimed is:

1. A particle stabilizing composition comprising:
   a. an emulsion comprising about 1% to about 99%, by weight of the emulsion, of an internal phase and from about 1% to about 99%, by weight of the emulsion, of an external phase;
   b. a first charged species which is selected form the group consisting of a first polyanion and a first polycation wherein said first species is present in the emulsion; and
   c. charged insoluble solid particles comprising titanium dioxide that are dispersed in said emulsion in the presence of a second charged species which is selected from the group consisting of a second polyanion and a second polycation;
   wherein the first or second polyanion is selected from the group consisting of ammonium polyacrylate, sodium polyacrylate, potassium polyacrylate, ethylene acrylic acid copolymer, and mixtures thereof,
   wherein the first or second polycation is selected from the group consisting of quaterniums, quaternium-80, quaternium-61, polyquaterniums, and mixtures thereof;
   wherein the first charged species possesses a charge opposed to that of the second charged species and of the charged insoluble solid particles and wherein essentially all of the charged species and charged insoluble solid particles accumulate at the interface of the emulsion and wherein Brownian motion is not exhibited by the insoluble solid particles.

2. The composition of claim 1 wherein said composition is in a product form selected from the group consisting of cosmetics, fabric care products, home care products, diapers, incontinence articles, feminine care products, pharmaceuticals, oral care products, antiperspirants, deodorants, personal cleansing products, skin care products, and hair care products.

3. The composition of claim 1 further comprising uncharged insoluble solid particles.

4. The composition of claim 1 wherein the composition comprises from about 5% to about 20%, by weight of the composition, of the charged insoluble solid particles.

* * * * *